(12) United States Patent
Turner et al.

(10) Patent No.: US 9,732,335 B2
(45) Date of Patent: *Aug. 15, 2017

(54) METHODS OF SCREENING FOR MICROORGANISMS THAT IMPART BENEFICIAL PROPERTIES TO PLANTS

(71) Applicant: Biodiscovery New Zealand Limited, Auckland (NZ)

(72) Inventors: Susan Jane Turner, Auckland (NZ); Peter John Wigley, Auckland (NZ)

(73) Assignee: BIODISCOVERY NEW ZEALAND LIMITED, Auckland (NZ)

(*) Notice: Subject to any disclaimer, the term of this patent is extended or adjusted under 35 U.S.C. 154(b) by 746 days.

This patent is subject to a terminal disclaimer.

(21) Appl. No.: 14/050,788

(22) Filed: Oct. 10, 2013

(65) Prior Publication Data

US 2014/0115731 A1    Apr. 24, 2014

Related U.S. Application Data

(63) Continuation of application No. 14/031,461, filed on Sep. 19, 2013, now abandoned.

(30) Foreign Application Priority Data

Sep. 19, 2012    (NZ) ........................................ 602534

(51) Int. Cl.
 *C12N 15/10* (2006.01)
(52) U.S. Cl.
 CPC ................................ *C12N 15/1058* (2013.01)
(58) Field of Classification Search
 CPC ................................................ C12N 15/1058
 See application file for complete search history.

(56) References Cited

U.S. PATENT DOCUMENTS

| | | | |
|---|---|---|---|
| 4,647,533 | A | 3/1987 | Weller et al. |
| 5,157,207 | A | 10/1992 | Carlson et al. |
| 5,415,672 | A | 5/1995 | Fahey et al. |
| 5,882,641 | A | 3/1999 | Shetty |
| 5,997,269 | A | 12/1999 | Feitelson |
| 7,232,565 | B2 | 6/2007 | Henson et al. |
| 7,723,576 | B2 | 5/2010 | Hawkes |
| 7,786,344 | B2 | 8/2010 | Kock et al. |
| 8,049,077 | B2 | 11/2011 | Leij |
| 8,642,843 | B2 | 2/2014 | Pallottini |
| 9,113,636 | B2 | 8/2015 | Von Maltzahn et al. |
| 9,150,851 | B2 | 10/2015 | Wigley et al. |
| 9,260,713 | B2 | 2/2016 | Wigley et al. |
| 9,365,847 | B2 | 6/2016 | Wigley et al. |
| 2003/0228679 | A1 | 12/2003 | Smith |
| 2012/0015806 | A1 | 1/2012 | Paikray et al. |
| 2012/0129794 | A1 | 5/2012 | Dowd et al. |
| 2012/0284852 | A1 | 11/2012 | Lindhout et al. |
| 2013/0005572 | A1 | 1/2013 | Levenfors et al. |
| 2014/0082770 | A1 | 3/2014 | Wigley et al. |
| 2014/0109249 | A1 | 4/2014 | Turner et al. |
| 2014/0115731 | A1 | 4/2014 | Turner et al. |
| 2015/0080261 | A1 | 3/2015 | Wigley et al. |
| 2015/0150161 | A1 | 5/2015 | Spangenberg et al. |
| 2015/0156982 | A1 | 6/2015 | Spangenberg et al. |
| 2015/0191720 | A1 | 7/2015 | Beilinson et al. |
| 2015/0218568 | A1 | 8/2015 | Jones et al. |
| 2015/0250116 | A1 | 9/2015 | Wigley et al. |
| 2015/0368637 | A1 | 12/2015 | Wigley et al. |
| 2016/0289667 | A1 | 10/2016 | Wigley et al. |
| 2017/0086402 | A1 | 3/2017 | Meadows-Smith et al. |

FOREIGN PATENT DOCUMENTS

| | | |
|---|---|---|
| NZ | 588048 | 3/2012 |
| WO | WO 2012/125050 A1 | 9/2012 |
| WO | WO 2013/177615 A1 | 12/2013 |
| WO | WO 2013/177616 A1 | 12/2013 |
| WO | WO 2014/046553 A1 | 3/2014 |
| WO | WO 2014/210372 A1 | 12/2014 |
| WO | WO 2015/035099 A1 | 3/2015 |
| WO | WO 2015/100432 A2 | 7/2015 |
| WO | WO 2015/105993 A1 | 7/2015 |
| WO | WO 2015/116838 A1 | 8/2015 |
| WO | WO 2015/142185 A1 | 9/2015 |
| WO | WO 2015/179825 A1 | 11/2015 |
| WO | WO 2016/130586 A2 | 8/2016 |
| WO | WO 2017/019633 A2 | 2/2017 |

OTHER PUBLICATIONS

U.S. Appl. No. 14/991,543, filed Jan. 8, 2016, Wigley et al.
Ahmad et al. "Screening of free-living rhizospheric bacteria for their multiple plant growth promoting activities." Microbiological Research, 163.2: 173-181 (2008).
European Patent Application No. 13838538.0, Extended European Search Report dated Apr. 11, 2016.
Hayat et al. "Soil beneficial bacteria and their role in plant growth promotion: a review." Annals of Microbiology, 60.4: 579-598 (2010).
Infantino, A. et al., "Screening techniques and sources of resistance to root diseases in cool season food legumes", *Euphytica*, 147: 201-221 (2006).
International Search Report and Written Opinion in International Application No. PCT/US2015/032278, mailed Aug. 26, 2015, 13 pages.
Khalid et al. "Screening plant growth-promoting rhizobacteria for improving growth and yield of wheat." Journal of Applied Microbiology, 96.3: 473-480 (2004).

(Continued)

*Primary Examiner* — Bin Shen
(74) *Attorney, Agent, or Firm* — Cooley LLP

(57) ABSTRACT

The invention relates to methods for the screening, identification and/or application of microorganisms of use in imparting beneficial properties to plants. In one embodiment, the method involves subjecting one or more plants to a growth medium in the presence of a set of microorganisms, selecting one or more plant, acquiring one or more microorganisms associated with the selected plant(s) and repeating the process one or more times. The method further involves the step of subjecting the one or more microorganisms to a conditioning and/or directed evolution process.

14 Claims, 1 Drawing Sheet

(56) References Cited

OTHER PUBLICATIONS

Figure 1:
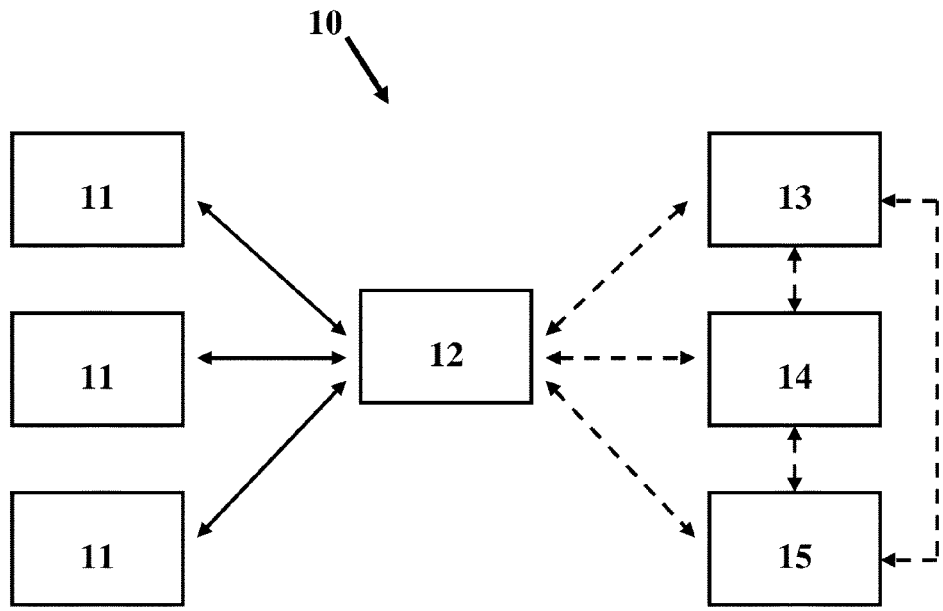

Mueller and Sachs, "Engineering Microbiomes to Improve Plant and Animal Health", Trends in Microbiology, TIMI 1227, 12 pages (2015). http://dx.doi.org/10.1016/j.tim.2015.07.009.
Panke-Buisse, P. et al., "Selection on soil microbiomes reveals reproducible impacts on plant function", The ISME Journal, 9: 980-989 (2015).
Taghavi et al. "Genome survey and characterization of endophytic bacteria exhibiting a beneficial effect on growth and development of poplar trees." Applied and Environmental Microbiology, 75.3: 748-757 (2009).
Zarraonaindia, I. et al., "The Soil Microbiome Influences Grapevine-Associated Microbiota", mBio(American Society for Microbiology), 6(2): e02527-14, pp. 1-10 (2015).
Colby, R.S., "Calculating Synergistic and Antagonistic Responses of Herbicide Combinations", Weeds, 15(1):20-22 (1967).
Gangwar, M. and Kaur, G., "Isolation and characterization of endophytic bacteria from endorhizosphere of sugarcane and ryegrass", The Internet Journal of Microbiology, 7(1):1-7 (2008).
Jiangen, L. et al., "Study on Isolation and Screening of Plant-growth Promoting Rhizobacteria and its Biocontrol Action to Soil-borne Diseases of Cucumber", Chinese Agricultural Science Bulletin, vol. 23, No. 12, (and English translation) (2007).
Saraf, M. et al., Chapter 13, "Perspectives of PGPR in Agri-Ecosystems", "Bacteria in Agrobiology: Crop Ecosystems," Springer, Dinesh K. Maheshwari, Editor, p. 361-385 (2011).
Stewart, Gordon S.A.B. et al., "Commitment of bacterial spores to germinate. A measure of the trigger reaction", Biochem. J., 198:101-106 (1981).
International Preliminary Report on Patentability in International Application No. PCT/NZ2013/000171, dated Mar. 24, 2015, 9 pages.
Chi, F. et al., "Ascending migration of endophytic rhizobia, from roots to leaves, inside rice plants and assessment of benefits to rice growth physiology", Applied and Environmerital Microbiology, 71(11):7271-7278 (2005).
Cook, R. James, "A customized approach to biological control of wheat root diseases", NATO ASI Series A Life Sciences; Biological Control of Plant Diseases: Progress and Challenges for the Future, Plenum Press, pp. 211-222 (1992).
Eckford, R. et al. , "Free-living heterotrophic bacteria isolated from fuel-contaminated Antarctic soils", Applied and Environmental Microbiology, 68(10):5181-5185 (2002).
Gordon, J.C. and Wheeler, C.T., "Biological Nitrogen Fixation in Forest Ecosystems: Foundations and Applications", Martinus Nijhoff/ Dr W. Junk Publishers, The Hague, pp. 102-105, ISBN 90-247-2849-5 (1983).
Gyaneshar, P. et al., "Herbaspirillum colonization increases growth and nitrogen accumulation in aluminum-tolerant rice varities", New Phytologist, 154:131-145 (2002).
Jetiyanon, K et al., "Film coating of seeds with Bacillus cereus RS87 spores for early plant growth enhancement", Canadian Journal of Microbiology, 54(10):861-887 (2008).
Ji, X et al., "Colonization of Morus alba L. by the plant-growth-promoting and antagonistic bacterium Burkholderia cepacia strain Lu10-1", BMC Microbiology, 10:243 (2010).
Johnsen, A.R., "Priming with bioremediated soil dominated by mycobacteria strongly impacted the PAH-degrader community of a PAH-polluted soil, but the effect on PAD-degradation was marginal", Applied and Environmental Microbioiogy, 73(5):1474-480 (2007).
Kamilova, F. et al., "Enrichment for competitive plant root tip colonizers selects for a new class of biocontrol bacteria", Environmental Microbiology, 7(11):1809-1817 (2005).
Kuiper, I. et al., "Selection of a plant-bacterium pair as a novel tool for rhizostimulation of polycyclic aromatic hydrocarbon-degrading bacteria", Molecular Plant—Microbe Interactions, American Pathological Society, USA. 14(10):1197-1205 (2001).

Lee, D.W. And Lee, S.D. "Aeromicrobium ponti sp. nov., isolated from seawater", International Journal of Systematic and Evolutionary Microbiology, 58:987-991 (2008).
Mehnaz, S. and Lazarovits, G. et al., "Inoculation effects of Pseudomonas putida, Gluconacetobacter azotocaptans, and Azospirillurn lipoferum on corn plant growth under greehouse conditions", Microbial Ecology, 51(3):326-335 (2006).
Pandey, P. et al., "Isolation of endophytic plant growth promoting Burkholderia sp. MSSP from root nodules of Mimosa pudica", Current Science, 89(1):177-180 (2005).
"Pikovskaya's Broth (medium): Pikovskaya's Broth is recommended for cultivation phosphate solubilizing microorganisms", M1719, HIMEDIA, Technical Data, 2 pages (2011).
"Pikovskayas Agar: Pikovskayas Agar is recommended for detection of phosphate-solubilizing soil microorganisms", M520, HIMEDIA, Technical Data, 2 pages (2011).
Pliego, C. et al., "Screening for candidate bacterial biocontrol agents against soilborne fungal plant pathogens", Plant Soil, 340(1-2):505-520 (2010).
Pliego, C. et al., "'Plant Growth-Promoting Bacteria: Fundamentals and Exploitation"; Bacteria in Agrobiology: Crop Ecosystems, Springer, USA, pp. 295-343 (2011).
Ryan. R.P. et al., "Bacterial endophytes: recent developments and applications", FEMS Microbiology Letters, 278.1-9 (2008).
Wu, J et al., "Rhizoctonia fungi enhance the growth of the endangered orchid Cymbidium goeringii", Botany, 88(1)20-29 (2010).
Yemm, E.W. and Willis, A.J., "The estimation of carbohydrates in plant extracts by anthrone", Biochem. J., 57:508-514 (1954).
Zhao, L.F. et al., "Colonization and plant growth promoting characterization of endophytic Pseudomonas chlororaphis strain Zong1 isolated from Sophora alopecuroides", Brazilian Journal of Microbiology, 44(2):623-631 (2013).
Zhao, L. et al., "identification and characterization of the endophytic plant growth prompter Bacillus cereus strain MQ23 isolated from Sophora alopecuroides root nodules", Brazilian Journal of Microbiology, 42:567-575 (2011).
Extended European Search, Report in EP Application No. 12757224.6 dated Aug. 6, 2014, 7 pages.
International Search Report in International Application No. PCT/NZ2012/000041 mailed Jul. 17, 2012, 5 pages.
Written Opinion in International Application No. PCT/NZ2012/000041, mailed July 17, 2012, 8 pages.
International Preliminary Report on Patentability in International Application No. PCT/NZ2012/000041, mailed Sep. 17, 2013, 2012, 9 pages.
International Search Report and Written Opinion in International Application No. PCT/NZ2013/000171, mailed Jan. 2, 2014, 14 pages.
International Search Report and Written Opinion in International Application No. PCT/NZ2014/000044, mailed May 21, 2014, 12 pages.
International Search Report and Written Opinion in International Application No. PCT/NZ2014/000045, mailed May 22, 2014, 12 pages.
[No Author Listed], Koch's Postulates. Wikipedia. http://en.wikipedia.org/wiki/Koch's_postulates [last accessed May 15, 2014].
Allen et al., The Leguminosae. A Source Book of Characteristics, Uses, and Nodulation. Macmillan Publishers Ltd. (Scientific and Medical Division), London and Basingstoke, UK, 1981, p. xvi, ISBN 0-333-32221-5.
Yanni et al., Natural endophytic association between Rhizobium leguminosarum bv. trifolii and rice roots and assessment of its potential to promote rice growth. Plant and Soil. 1997; 194: 99-114.
Bacon et al., (1997) Isolation and culture of endophytic bacteria. In Hurst et al (Eds), Manual of Environmental Microbiology, 1997 ASM Press, Washington DC, Chapter 45, pp. 413-421.
Elo et al., (2000) Humus bacteria of Norway spruce stands: plant growth promoting properties and birch, red fescue and alder colonizing capacity Microbiology Ecology 31:143-152.
Fahraeus, (1957) The infection of clover root hairs by nodule bacteria studied by a simple glass slide technique J .Gen Microbiol. 16:374-381.

(56) References Cited

OTHER PUBLICATIONS

Johnsen et al., (2007) Strong Impact on the Polycyclic Aromatic Hydrocarbon (PAH)-Degrading Community of a PAH-Polluted Soil but Marginal Effect on PAH Degradation when Priming with Bioremediated Soil Dominated by Mycobacteria, *Applied and Envrionmental Microbiology* 73(5): 1474-480.

Martani et al., "Isolation and Selection of Rhizobium Tolerant to Pesticides and Aluminium from Acid Soils in Indonesia", Journal of Tropical Soils, 2011, vol. 16, No. 1, pp. 47-54.

Miche et al.. (2001) Effects of rice seed surface sterilization with hypocholorite on inoculated *Burkholderiavietamiensis*. Appl Environ Microbiol. 67(7): 3046-3052.

Murashige et al., (1962) A revised medium for rapid growth and bioassays with tobacco tissue cultures. Physiol Plant 15(3): 473:497.

No Author Listed, "Directed Evolution" from Wikipedia, the free encyclopedia, see http://en.wikipedia.org/wiki/Directed_evolution, Mar. 5, 2012, 4 pages.

No Author Listed, Forum for Nuclear Cooperation in Asia (FNCA) Biofertilizer Project Group (2006). *Biofertilizer Manual.* Tokyo: Japan Atomic Industrial Forum (JAIF), 138 pages.

Pikovskaya, (1948) Phosphate mobilization in soils as related to life processes of some microorganisms *Microbiologiya* 17:362-370.

Rao et al., "Pattern of modulation and nitrogen fixation in mothbean", Indian Journal of Agricultural Science, 1983, vol. 53, No. 12, pp. 1035-1038.

Rodriguez et al., "Stress tolerance in plants via habitat-adapted symbiosis", The ISME Journal, 2008, vol. 2, pp. 404-416.

Scholthof, (2001) Molecular plant-microbe interactions that cut the mustard *Plant Physiology* 127: 1476-1483.

Singer et al., (2005) Perspectives and vision for strain selection in bioaugmentation *Trends in Biotechnology* 23(2):74-77; Available online Dec. 24, 2004.

Strobel et al., (2003) Bioprospecting for microbial endophytes and their natural products. *Microbiology and Molecular Biology Reviews* 67(4):491-502.

Venkateswarlu, "Nitrogen fixation in Arid and Semi-arid agriculture: Opportunities and Constraints" in Agricultural Nitrogen Use & Its Environmental Implications. Edited by Y.P. Abrol et al., I.K. International Publishing House, New Delhi. 2007, Chapter 20, pp. 415-436.

Zinniel et al., (2002) Isolation and characterisation of endophytic colonising bacteria from agronomic crops and prairie plants *Applied and Environmental Microbiology* 68(5):2198-2208.

"Acinetobacter", MicrobeWiki, available at https://microbewiki.kenyon.edu/index.php/Acinetobacter, Apr. 13, 2015, 4 pages.

"Arthrobacter", MicrobeWiki, available at https://microbewiki.kenyon.edu/index.php/Arthrobacter, Sep. 14, 2015, 3 pages.

"Pantoea agglomerans", https://en.wikipedia.org/wiki/Pantoea_agglomerans, Jan. 24, 2017, 3 pages.

Australian Patent Application No. AU 2012229598, Third Party Observation filed Feb. 1, 2017, 18 pages.

Choi, Jung-Hye, et al. "*Acidovorax soli* sp. nov., isolated from landfill soil." International Journal of Systematic and Evolutionary Microbiology (2010); 60.12: 2715-2718.

Easlon, Hsien Ming, and Richards, James, H. "Drought response in self-compatible species of tomato (*Solanaceae*)." American Journal of Botany (2009); 96.3: 605-611.

European Patent Application No. 12757224.6 (EP 2685807) in the name of Bioconsortia, Inc., Third Party Observation filed Jan. 24, 2017, 9 pages.

European Patent Application No. 12757224.6 (EP 2685807) in the name of Bioconsortia, Inc., EPO Communication dated Jan. 30, 2017, 86 pages, concerning Third Party Observation filed Jan. 24, 2017.

European Patent Application No. 13838538.0 (EP 2898060) in the name of Bioconsortia, Inc., Third Party Observation filed Jan. 26, 2017, 8 pages.

European Patent Application No. 13838538.0 (EP 2898060) in the name of Bioconsortia, Inc., EPO Communication dated Feb. 6, 2017, 101 pages, concerning Third Party Observation filed Jan. 26, 2017.

Ghnaya, Asma Ben, et al. "Polyamine levels and pigment contents in rapeseed regenerated in vitro in the presence of zinc." Journal of Environmental Chemistry and Ecotoxicology (2011); 3.8: 206-213.

Koransky, Jack R., et al. "Use of ethanol for selective isolation of sporeforming microorganisms." Applied and Environmental Microbiology (1978); 35.4: 762-765.

Li, Dan. "Phenotypic variation and molecular signaling in the interaction of the rhizosphere bacteria *Acidovorax* sp. N35 and Rhizobium radiobacter F4 with roots." Dissertation 2011; LMU Munchen: Faculty of Biology [retrieved on Jun. 20, 2016 from https://edoc.ub.uni-muenchen.de/12657/], 125 pages.

Monje, David M.J., "Microbial ecology of endophytic bacteria in *Zea* species as influenced by plant genotype, seed origin, and soil environment." Thesis, The University of Guelph, May 2011, 20 pages.

Orlando, Roberto, et al. "Pectic enzymes as a selective pressure tool for in vitro recovery of strawberry plants with fungal disease resistance." Plant Cell Reports (1997); 16.5: 272-276, 2 pages (Summary Only).

Park, Myung Soo, et al. "Isolation and characterization of bacteria associated with two sand dune plant species, *Calystegia soldanella* and *Elymus mollis*." Journal of Microbiology (2005); 43(3): 219-227.

Rokhbakhsh-Zamin, Farokh, et al. "Characterization of plant-growth-promoting traits of *Acinetobacter* species isolated from rhizosphere of Pennisetum glaucum." J Microbiol Biotechnol (2011); 21.6: 556-566.

Ryan, Robert P., et al. "The versatility and adaptation of bacteria from the genus *Stenotrophomonas*." Nature Reviews Microbiology (2009); 7.7: 514-525.

Yu, X., et al., Genbank Accession FJ455451. Publication [online]. Dec. 10, 2008 [retrieved Mar. 22, 2017] https://www.ncbi.nlm.nih.gov/nuccore/215882158?sat=4&satkey=26389799, 2 pages.

International Preliminary Report on Patentability in International Application No. PCT/US2015/032278, mailed Nov. 29, 2016, 11 pages.

International Search Report and Written Opinion in International Application No. PCT/US2016/017204, mailed Aug. 10, 2016, 13 pages.

International Search Report and Written Opinion in International Application No. PCT/US2016/043933, mailed Jan. 26, 2017, 14 pages.

Egamberdieva and Kucharova, "Selection for root colonizing bacteria stimulating wheat growth in saline soils", *Biol Fertil Soils*, 45: 563-571 (2009).

Kim, Yeon-Ju et al., "*Microbacterium ginsengiterrae* sp. nov., a β-glucosidase-producing bacterium isolated from soil of a ginseng field", *International Journal of Systematic and Evolutionary Microbiology*, 60(12):2808-2812 (2010).

Kirchhof, G. et al., "*Herbaspirillum frisingense* sp. nov., a new nitrogen-fixing bacterial species that occurs in C4-fibre plants", *International Journal of Systematic and Evolutionary Microbiology*, 51(1):157-168 (2001).

Mavingui et al., "Generation of *Rhizobium* strains with improved symbiotic properties by random DNA amplification (RDA)", *Nature Biotechnology*, 15: 564-569 (1997).

Swenson et al., "Artificial ecosystem selection", *PNAS*, 97(16): 9110-9114 (2000).

Takeuchi, M. et al., "Taxonomic study of bacteria isolated from plants: proposal of *Sphingomonas rosa* sp. nov., *Sphingomonas pruni* sp. nov., *Sphingomonas asaccharolytica* sp. nov., and *Sphingomonas mali* sp. nov.", *International Journal of Systematic Bacteriology*, 45(2):334-341 (1995).

Mishra, Sanjeet, et al. "Evaluation of inoculum addition to stimulate in situ bioremediation of oily-sludge-contaminated soil." Applied and Environmental Microbiology (2001); 67.4: 1675-1681.

Cook, R. James. "The influence of rotation crops on take-all decline phenomenon." Phytopathology (1981); 71.2: 189-192.

(56) References Cited

OTHER PUBLICATIONS

De Deyn, et al. "Plant functional traits and soil carbon sequestration in contrasting biomes." Ecology Letters (2008); 11.5: 516-531.
Gage, D.J., et al., "Use of Green Fluorescent Protein to Visualize the Early Events of Symbiosis between Rhizobium meliloti and Alfalfa (Medicago sativa)." Journal of Bacteriology (1996); 178(24): 7159-7166.
Moawad, H. A., et al., "Rhizosphere Response as a Factor in Competition Among Three Serogroups of Indigenous Rhizobium japonicum for Nodulation of Field-Grown Soybeans." Applied and Environmental Microbiology (1984); 47.4: 607-612.
Vessey, J. Kevin, et al. "Root-based $N_2$-fixing symbioses: Legumes, actinorhizal plants, *Parasponia* sp. and cycads." Plant and Soil (2005); 274.1-2: 51-78.

METHODS OF SCREENING FOR MICROORGANISMS THAT IMPART BENEFICIAL PROPERTIES TO PLANTS

RELATED APPLICATION

This application is a continuation of U.S. application Ser. No. 14/031,461, filed on Sep. 19, 2013, which claims priority from New Zealand Provisional Application No. 602534, filed Sep. 19, 2012, the content of which is hereby incorporated by reference herein.

FIELD

The present invention relates to methods for the screening, identification and/or application of microorganisms of use in imparting beneficial properties to plants.

BACKGROUND

Geography, environmental conditions, disease and attack by insects are major factors influencing the ability to grow and cultivate different species of plant. Such factors can have a significant downstream economic and social impact on communities around the world. There would be benefit in identifying products and methods which might impart beneficial properties to a plant species to allow it to grow in a variety of geographical locations, in different weather conditions, to survive disease and to be resistant to attack by insects, for example.

There is an ever increasing demand for plants having other desirable characteristics such as improved quality, increased or decreased levels of certain compounds, improved or different taste, smell, colour or other physical or chemical properties.

Selective breeding techniques have been used to this end. Selective breeding relies principally on genetic diversity in a starting population coupled with selection to achieve a plant cultivar with characteristics beneficial for human use. As the available, unused genetic diversity of cultivatable plant species has diminished, the potential for improvement has decreased. This situation has stimulated the growth of plant genetic modification in which genes from closely related species are introgressed into the new cultivar to provide a new genetic base for imparting desirable traits into new cultivars. However, this process is extremely costly, slow, limited in its scope and fraught with regulatory difficulties. Few commercial successes have eventuated from over two decades of large-scale investment into this technology.

Despite many decades of successful scientific research into the conventional breeding of highly-productive crops and into development of transgenic crops, relatively little research effort has been directed at development of plant traits via other means.

The importance of providing "good" soil with a rich microbial diversity via composts, complex biomaterial fertilisers e.g. blood and bone, to plants to ensure their healthy growth has been understood by home gardeners' and producers of organic foods. However, the inventors have recognised that the complexity of the plant-microorganism associations that underpin the observable benefits is poorly understood. Benefits to plant growth and health in such soils are often microbially-mediated through improved nutrient availability. This may be the result of solubilisation of minerals from the soil biomass itself, or from colonization of the plants with microorganisms in endophytic, epiphytic or rhizospheric associations leading to nitrogen fixation, resistance to pests and diseases through direct microbial competition within the plant, or the elicitation of plant defence reactions. The science community has produced literature on the diverse mechanisms of endophytic, epiphytic and rhizospheric plant microorganism associations, largely in relation to crop plants and their soils. The nature of some associations is known, encompassing the genetic basis of plant-induced metabolite production by specific organisms and the reverse influence of the microbe on gene expression in the plant (e.g. *Neotyphodium* spp), and increases in plant growth following microbial application to certain crop plants or seeds has been documented. However, despite the potential of microorganisms to improve plant growth, commercial success is limited to a relatively small range of specific microbial applications e.g. *Rhizobium* spp. to legume seeds, or the use of products resulting from "uncontrolled" microbial fermentations e.g. compost teas, seaweed fermentations, fish waste fermentations etc.

There are many specific strains of potentially beneficial microorganisms for association with specific plant cultivars, making the task of finding an appropriate strain(s) for any particular crop a very onerous procedure. Current means primarily focus on the application of microorganisms singly or in limited combinations. Such microorganisms are likely to have been selected for specific potential properties based on their identity. It would be useful if there was no requirement for knowledge of microbial identity for success.

Bibliographic details of the publications referred to herein are collected at the end of the description.

OBJECT

It is an object of the present invention to provide a method for the selection of one or more microorganism and/or composition which is of use in imparting one or more beneficial property to a plant which overcomes or ameliorates at least one of the disadvantages of known methods.

Alternatively it is an object of the invention to provide a method and/or system for assisting in the improvement of one or more plants.

Alternatively, it is an object to at least provide the public with a useful choice.

STATEMENT OF INVENTION

In a first broad aspect of the present invention there is provided a method for the selection of one or more microorganisms capable of imparting one or more beneficial property to a plant, the method comprising at least the steps of:
  a) subjecting one or more plant (including for example seeds, seedlings, cuttings, and/or propagules thereof) to a growth medium in the presence of a first set of one or more microorganisms;
  b) selecting one or more plant following step a);
  c) acquiring a second set of one or more microorganisms associated with said one or more plant selected in step b);
  d) repeating steps a) to c) one or more times, wherein the second set of one or more microorganisms acquired in step c) is used as the first set of microorganisms in step a) of any successive repeat; and,
wherein the first set of one or more microorganisms has been subjected to one or more of a conditioning and a directed evolution process prior to step a) and/or the second set of one or more microorganisms acquired in step c) is subjected to one or more of a conditioning and a directed evolution process prior to being used in step a) of any successive repeat.

In one embodiment, the second set of one or more microorganisms are isolated from said one or more plant in step c).

In one embodiment, where two or more microorganisms are acquired in step c), the method further comprises the steps of separating the two or more microorganisms into individual isolates, selecting two or more individual isolates, and then combining the selected two or more isolates.

In another embodiment, the method further comprises repeating steps a) to c) one or more times, wherein where two or more microorganisms are acquired in step c), the two or more microorganisms are separated into individual isolates, two or more individual isolates are selected and then combined, and the combined isolates are used in step a) of the successive repeat. Accordingly, where reference is made to using the one or more microorganisms acquired in step c) in step a) of the method, it should be taken to include using the combined isolates of this embodiment of the invention.

In another embodiment, two or more methods of the invention may be performed separately and the one or more microorganisms acquired in step c) of each separate method combined. In one embodiment, the combined microorganisms are used in step a) when performing a further method of the invention.

In a second broad aspect of the present invention there is provided a method for the selection of one or more microorganisms capable of imparting one or more beneficial property to a plant, the method comprising at least the steps of:
  a) subjecting one or more plant (including for example seeds, seedlings, cuttings, and/or propagules thereof) to a growth medium in the presence of a first set of one or more microorganisms;
  b) applying one or more selective pressure during step a);
  c) selecting one or more plant following step b); and,
  d) acquiring a second set of one or more microorganisms associated with said one or more plant selected in step c); and,
wherein the first set of one or more microorganisms has been subjected to one or more of a conditioning and a directed evolution process prior to step a) and/or the second set of one or more microorganisms acquired in step d) are subjected to one or more of a conditioning and a directed evolution process.

In a related (but distinct) second broad aspect of the present invention there is provided a method for the selection of one or more microorganisms capable of imparting one or more beneficial property to a plant, the method comprising at least the steps of:
  a) subjecting one or more plant (including for example seeds, seedlings, cuttings, and/or propagules thereof) to a growth medium in the presence of a first set of one or more microorganisms;
  b) applying one or more selective pressure during step a);
  c) selecting one or more plant following step b); and,
  d) acquiring a second set of one or more microorganisms associated with said one or more plant selected in step c); and,
  e) repeating steps a) to d) one or more times, wherein the second set of one or more microorganisms in step d) is used as the first set of one or more microorganisms in step a) of any successive repeat; and,
wherein the first set of one or more microorganisms has been subjected to one or more of a conditioning and a directed evolution process prior to step a) and/or the second set of one or more microorganisms acquired in step d) are subjected to one or more of a conditioning and a directed evolution process.

In such an embodiment, the second set of one or more microorganisms acquired in step d) may be subjected to one or more of a conditioning and a directed evolution process prior to being used in step a) of any successive repeat of the method.

In one embodiment, the second set of one or more microorganisms are isolated from said one or more plant in step d).

In one embodiment, one selective pressure is applied in step b).

In one embodiment, the selective pressure is biotic and includes but is not limited to exposure to one or more organisms that are detrimental to the plant. In one embodiment, the organisms include fungi, bacteria, viruses, insects, mites and nematodes.

In another embodiment, the selective pressure is abiotic. Abiotic selective pressures include, but are not limited to, exposure to or changes in the level of salt concentration, temperature, pH, water, minerals, organic nutrients, inorganic nutrients, organic toxins, inorganic toxins, and metals.

In one embodiment, the selective pressure is applied during substantially the whole time during which the one or more plant is subjected to the growth medium and one or more microorganisms. In one embodiment, the selective pressure is applied during substantially the whole growth period of the one or more plant. Alternatively, the selective pressure is applied at a discrete time point.

In one embodiment, where two or more microorganisms are acquired in step d), the method further comprises the steps of separating the two or more microorganisms into individual isolates, selecting two or more individual isolates, and then combining the selected two or more isolates.

In another embodiment, the method further comprises repeating steps a) to d) one or more times, wherein the one or more microorganisms acquired in step d) are used in step a) of any successive repeat.

In another embodiment, the method further comprises repeating steps a) to d) one or more times, wherein where two or more microorganisms are acquired in step d), the two or more microorganisms are separated into individual isolates, two or more individual isolates are selected and then combined, and the combined isolates are used in step a) of any successive repeat. Accordingly, where reference is made to using the one or more microorganisms acquired in step d) in step a) of the method, it should be taken to include using the combined isolates of this embodiment of the invention.

In one embodiment, one or more selective pressure applied in any successive repeats of steps a) to d) is different. In another embodiment, the selective pressure(s) applied in any successive repeats of steps a) to d) is the same.

In one embodiment, the method further comprises the following step which is conducted prior to step a): subjecting the one or more plant (including for example seeds, seedlings, cuttings, and/or propagules thereof) to a growth medium in the presence of one or more microorganisms, and after a desired period, acquiring one or more microorganisms associated with said one or more plant. In a preferred embodiment, the acquired one or more microorganisms are used in step a) of the process. In one embodiment, this step may be conducted two or more times prior to step a).

In another embodiment, two or more methods of the invention may be performed separately and the one or more microorganisms acquired in step d) of each separate method combined. In one embodiment, the combined microorganisms are used in step a) when performing a further method of the invention.

In one embodiment of the first aspect or second (and/or related) aspect, the methods are combined, in any order or combinations. In one embodiment, the method comprises:

1. a) subjecting one or more plant (including for example seeds, seedlings, cuttings, and/or propagules thereof) to a growth medium in the presence of a first set of one or more microorganisms;
   b) selecting one or more plant following step a);
   c) acquiring a second set of one or more microorganisms associated with said one or more plant selected in step b);
   and,
2. a) subjecting one or more plant (including for example seeds, seedlings, cuttings, and/or propagules thereof) to a growth medium in the presence of a the second set of one or more microorganisms acquired in step 1 c);
   b) applying one or more selective pressure during step 2 a);
   c) selecting one or more plant following step 2 b); and,
   d) acquiring a second set of one or more microorganisms associated with said one or more plant selected in step 2 c).

Such a method may be repeated any number of times, wherein the one or more microorganisms acquired in step 2 d) are used in step 1 a) of any successive repeats of the method. In another embodiment, the method comprises:

1. a) subjecting one or more plant (including for example seeds, seedlings, cuttings, and/or propagules thereof) to a growth medium in the presence of a first set of one or more microorganisms;
   b) applying one or more selective pressure during step a);
   c) selecting one or more plant following step b); and,
   d) acquiring a second set of one or more microorganisms associated with said one or more plant selected in step c); and,
2. a) subjecting one or more plant (including for example seeds, seedlings, cuttings, and/or propagules thereof) to a growth medium in the presence of the second set of microorganisms acquired in step 1 d);
   b) selecting one or more plant following step 2 a);
   c) acquiring a second set of one or more microorganisms associated with said one or more plant selected in step 2 b).

Such a method may be repeated any number of times, wherein the one or more microorganisms acquired in step 2 c) are used in step 1 a) of any successive repeats of the method. In other embodiments, steps 1 or 2 may be repeated one or more times before the microorganisms acquired in those steps are used in step 1 a) or step 2 a), as the case may be. In certain embodiments, where two or more microorganisms are acquired in steps 1 and/or 2, the methods may further comprise the step of separating the two or more microorganisms into individual isolates, selecting two or more individual isolates, and then combining the selected two or more isolates. The combined isolates may then be used in any successive repeats of the method or any part thereof. In addition, two or more methods or parts thereof may be performed separately and the one or more microorganisms acquired in steps 1 and/or 2 of the method combined. In one embodiment, the combined microorganisms are used in any successive rounds of the method or part thereof.

In one embodiment of the first or second (and/or related) aspect, the first set and/or second set of one or more microorganisms are selected from the microorganisms detailed herein after.

In one embodiment of the first or second (and/or related) aspect, the growth medium is selected from the growth media detailed herein after.

In one embodiment of the first or second (and/or related) aspect, the step of subjecting one or more plant to a growth medium involves growing or multiplying the plant.

In one embodiment of the first or second (and/or related) aspect, two or more plants are subjected to a growth medium in the presence of one or more microorganisms. In other embodiments 10 to 20 plants are subjected to a growth medium in the presence of one or more microorganisms. In other embodiments, 20 or more, 100 or more, 300 or more, 500 or more, or 1000 or more plants are subjected to a growth medium in the presence of one or more microorganisms.

In one embodiment of the first or second (and/or related) aspect, the one or more plant is selected on the basis of one or more selection criterion. In one embodiment, the one or more plant is selected on the basis of one or more phenotypic trait. In one preferred embodiment, the one or more plant is selected based on the presence of a desirable phenotypic trait. In one embodiment, the phenotypic trait is one of those detailed herein after. In one embodiment, the one or more plant is selected on the basis of one or more genotypic trait. In one preferred embodiment, the one or more plant is selected based on the presence of a desirable genotypic trait. In one embodiment, the one or more plant is selected based on a combination of one or more genotypic and one or more phenotypic traits. In one embodiment, different selection criteria may be used in each iteration of a method of the invention.

In one embodiment of the first or second (and/or related) aspect, the second set of one or more microorganisms are isolated from the root, stem and/or foliar (including reproductive) tissue of the one or more plants selected. Alternatively, the second set of one or more microorganisms are isolated from whole plant tissue of the one or more plants selected. In another embodiment, the plant tissues may be surface sterilised and then one or more microorganisms isolated from any tissue of the one or more plants. This embodiment allows for the targeted selection of endophytic microorganisms. In another embodiment, the second set of one or more microorganisms may be isolated from the growth medium surrounding selected plants.

In another embodiment of the first or second (and/or related) aspect, the second set of one or more microorganisms are acquired in crude form and may be used in used in step a) of any successive repeat.

In one embodiment of the first or second (and/or related) aspect, the one or more microorganisms are acquired any time after germination of the one or more plants.

In one embodiment, the methods of the first or second (and/or related) aspect of the invention may also be useful in identifying and/or selecting one or more endophytic microorganism capable of imparting one or more beneficial property to a plant.

In one embodiment, plant material (including for example seeds, seedlings, cuttings, and/or propagules thereof) may be used as the source of microorganisms for step a). In a preferred embodiment, the plant material used as a source for microorganisms in step a) is seed material. Preferably, the plant material is surface sterilised.

In another embodiment, the methods of the first or second (and/or related) aspect of the invention may be useful in identifying and/or selecting one or more unculturable microorganism capable of imparting one or more beneficial property to a plant. In this embodiment, plant material (including for example seeds, seedlings, cuttings, and/or propagules thereof) may be used as the source of microorganisms for step a). In a preferred embodiment, the plant material used as a source for microorganisms in step a) is explant material (for example, plant cuttings). Preferably, the plant material is surface sterilised.

In a third broad aspect, there is provided a method for assisting in the improvement of one or more plants, comprising arranging for the evaluation of said plant(s) in the presence of one or more microorganisms and/or compositions. The method preferably comprises at least the steps of a method of the first, second (and/or related), eighth (and/or related) and/or ninth (and/or related) aspects of the invention.

According to one embodiment, the plant(s) are for growing in a first region. The microorganism(s) may or may not (or at least to a significant extent) be present in the first region.

"Region" and "first region" are to be interpreted broadly as meaning one or more areas of land. The land areas may be defined by geographical/political/private land boundaries or by land areas having similar properties such as climate, soil properties, presence of a particular pest etc.

Preferably, the evaluation is performed in a second region in which the microorganism(s) are present, but this is in no way essential. Microorganisms may be obtained from other sources including microorganism depositaries and artificially associated with plant material and/or soil. Furthermore, while plant(s) may be cultivated in essentially a conventional manner (but, in one particular embodiment in a region having microorganisms not normally associated with the plant(s)), at least in the first region, artificial growing environments may alternatively be used as would be appreciated by those skilled in the art. Thus, possible beneficial microorganism/plant relationships may be identified that would not necessarily normally be utilised.

Preferably, the step of arranging comprises arranging for one or more of:
  receipt or transmission of an identity of one or more plants or plant types to be evaluated;
  receipt or transmission of plant material from one or more plants or plant types to be evaluated;
  identification and/or selection of the microorganism(s) and/or composition(s);
  acquisition of the microorganism(s) and/or composition(s); and
  associating the microorganism(s) and/or composition(s) with the plant material.

Preferably, the method comprises evaluating (or arranging for said evaluation of) said plant(s) in the presence of said microorganism(s) and/or composition(s).

The step of evaluating preferably comprises performing one or more of the steps of a method described herein, in particular embodiments a method of the first aspect, second (and/or related) aspect, eighth (and/or related) aspect or ninth (and/or related) aspect of the invention.

The various steps identified above may be performed by a single entity although it is preferred that at least two parties are involved, a first which makes a request and a second which actions the request. Note that various agents may act for one or both parties and that varying levels of automation may be used. For example, in response to a particular request the microorganism(s) may be selected by a processor querying a database based on known microorganism associations for that or similar plant(s) with little or no input required from an operator.

Furthermore, the evaluation may be performed by the requesting party and/or in the first region. Performing the evaluation in the first region better ensures that the evaluation is accurate and that no unforeseen environmental factors that may impact on the plant(s) or the microorganism(s) are not considered.

Following the evaluation or during the course thereof, the method preferably further comprises one or more of:
  receiving or sending one or more microorganisms (or at least the identity thereof) and/or composition(s) to the first region, including in combination with plant material; and
  growing said plant(s) or other plants (preferably having similar properties) in the first region in the presence of said microorganism(s) and/or composition(s).

The method of the third aspect may be embodied by a first party:
  identifying a need for an improvement in a plant(s);
  sending the identity thereof and/or relevant plant material to a second party together with any relevant information, and
  receiving plant material and/or one or more microorganisms and/or the identities thereof and/or composition(s).

The step of receiving is preferably performed following or as a result of an assessment of plant/microorganism and/or plant/composition associations. Preferably, the assessment is made using a method as described herein, in particular embodiments a method of the first aspect, second aspect (and/or related), the eighth (and/or related) aspect or the ninth (and/or related) aspect.

The method of the third aspect may additionally or alternatively be embodied by a second party:
  receiving an identity of a plant(s) and/or relevant plant material from a first party together with any relevant information, and
  sending plant material and/or one or more microorganism(s) and/or the identities thereof and/or composition(s) to the first party.

The step of sending is preferably performed following or as a result of an assessment of plant/microorganism and/or plant/composition associations. Preferably, the assessment is made using a method described herein, in particular embodiments a method of the second aspect (and/or related), the eighth (and/or related) aspect or the ninth (and/or related) aspect.

According to a fourth aspect, there is provided a system for implementing the method of the third aspect.

The system of the fourth aspect preferably includes one or more of:
  means for receiving or transmitting an identity of one or more plants or plant types to be evaluated;
  means for receiving or transmitting plant material from one or more plants or plant types to be evaluated;
  means for identifying and/or selecting microorganism(s) and/or composition(s);
  means for acquiring the microorganism(s) and/or composition(s);
  means for associating the microorganism(s) and/or composition(s) with the plant material;
  means for evaluating said plant(s) in the presence of said microorganism(s) and/or composition(s);

means for receiving or sending one or more microorganisms (or at least the identity thereof) and/or composition(s) to the first region, including in combination with plant material; and means for growing said plant(s) or other plants (preferably having similar properties) in the first region in the presence of said microorganism(s) and/or composition(s).

Means known to those skilled in the art may be used to provide the functionality required in the system of the third aspect. For example, conventional communication means, including the internet, may be used to convey the identities of plants/microorganisms; conventional carrier means may be used to convey the plant material/microorganisms/composition(s); conventional means and processes may be used to associate a microorganism and/or composition with plant material and conventional means for evaluating said plant(s) and/or the plant/microorganism and/or plant/composition associations may be used.

According to a preferred embodiment, the system of the invention is embodied by a facility configured to transmit request(s) for an improvement in a plant(s) and subsequently to receive plant material and/or one or more microorganisms and/or the identities thereof, preferably following or as a result of an assessment of plant/microorganism associations. Preferably, the assessment is made using a method described herein, in particular embodiments a method of the first aspect, the second aspect (and/or related), the eighth (and/or related) aspect, or the ninth (and/or related) aspect.

The system of the fourth aspect may additionally or alternatively be embodied by a facility configured to receive an identity of a plant(s) and/or relevant plant material from together with any relevant information; and send plant material and/or one or more microorganisms and/or the identities thereof and/or composition(s), preferably following or as a result of an assessment of plant/microorganism or plant/composition associations. Preferably, the assessment is made using a method described herein, in particular embodiments a method of the first aspect, the second aspect (and/or related), the eighth (and/or related) aspect or the ninth (and/or related) aspect.

Accordingly to a fifth broad aspect of the invention, there is provided a microorganism acquired, selected or isolated by a method as herein before described. In one embodiment, the microorganism is an endophyte. In one embodiment, the microorganism is unculturable.

In a sixth broad aspect of the invention, there is provided a method for the production of a composition to support plant growth, quality and/or health, or a composition to suppress or inhibit the growth, quality and/or health of a plant the method comprising the steps of a method herein before described and the additional step of combining the one or more microorganisms selected by the method with one or more additional ingredients.

In a seventh broad aspect of the invention, there is provided a composition comprising one or more microorganism of the fifth broad aspect or as prepared by a method of the sixth broad aspect.

In an eighth broad aspect of the invention there is provided a method for the selection of a composition which is capable of imparting one or more beneficial property to a plant, the method comprising at least the steps of:
  a) culturing one or more microorganisms selected by a method of the first aspect and/or second (and/or related) aspect in one or more media to provide one or more culture;
  b) separating the one or more microorganism from the one or more media in the one or more culture after a period of time to provide one or more composition substantially free of microorganisms;
  c) subjecting one or more plant (including for example seeds, seedlings, cuttings, and/or propagules thereof) to the one or more composition of step b);
  d) selecting one or more composition from step c) if it is observed to impart one or more beneficial property to the one or more plants.

In an aspect of the invention related (but distinct) to the eighth broad aspect of the invention there is provided a method for the selection of a composition which is capable of imparting one or more beneficial property to a plant, the method comprising at least the steps of:
  a) culturing one or more microorganisms selected by a method of the first aspect and/or the second (and/or related) aspect of the invention in one or more media to provide one or more culture;
  b) inactivating the one or more culture of step a) to provide one or more composition containing one or more inactivated microorganisms;
  c) subjecting one or more plant (including for example seeds, seedlings, cuttings, and/or propagules thereof) to the one or more composition of step b);
  d) selecting one or more composition from step c) if it is observed to impart one or more beneficial property to the one or more plants.

In a ninth broad aspect of the invention there is provided a method for the selection of one or more microorganisms which are capable of producing a composition which is capable of imparting one or more beneficial property to a plant, the method comprising at least the steps of:
  a) culturing one or more microorganism selected by a method of the first aspect and/or the second (and/or related) aspect in one or more media to provide one or more culture;
  b) separating the one or more microorganism from the one or more media in the one or more culture from step a) after a period of time to provide one or more composition substantially free of microorganisms;
  c) subjecting one or more plant (including for example seeds, seedlings, cuttings, and/or propagules thereof) to the one or more composition from step b);
  d) selecting the one or more microorganisms associated with (or in other words used to produce the) one or more composition observed to impart one or more beneficial property to the one or more plants.

In an aspect related (but distinct) to the ninth broad aspect of the invention there is provided a method for the selection of one or more microorganisms which are capable of producing a composition which is capable of imparting one or more beneficial property to a plant, the method comprising at least the steps of:
  a) culturing one or more microorganism in one or more media to provide one or more culture;
  b) separating the one or more microorganism from the one or more media in one or more culture after a period of time to provide one or more composition substantially free of microorganisms;
  c) subjecting one or more plant (including for example seeds, seedlings, cuttings, and/or propagules thereof) to the one or more composition of step b);
  d) selecting the one or more microorganisms associated with (or in other words used to produce the) one or more composition observed to impart one or more beneficial property to the one or more plants; and, e) using the one or more microorganisms selected in step d) in step a) of a method of the first or second or eighth or ninth aspects of the invention.

In a related aspect, step b) of the method of the ninth (and/or related) aspect could be substituted with the step of b) inactivating the one or more culture of step a) to provide one or more composition containing one or more inactivated microorganisms, and then using this composition in step c) of the process.

It should be appreciated that the methods of the first, second (and/or related), eighth (and/or related) and ninth (and/or related) aspects may be combined in any combination, including the methods being run concurrently or sequentially in any number of iterations, with compositions and/or microorganisms selected, acquired or isolated from the methods being used individually or combined and used in iterative rounds of any one of the methods. By way of example, a method of the eighth (and/or related) aspect may be performed and a composition selected. The selection of a composition indicates that the one or more microorganism separated from the media in step b) is desirable for imparting beneficial properties to the one or more plant (as the one or more microorganism is capable of producing a selected composition). The one or more microorganism may then be used in another round of a method of the first aspect, second (and/or related) aspect, eighth (and/or related) aspect or ninth (and/or related) aspect. Alternatively, the combination of methods could be run in reverse. This could be repeated any number of times in any order and combination. Accordingly, the invention provides for the use of one or more microorganism, composition or plant acquired, selected or isolated by a method of the invention in any other method of the invention.

In a tenth broad aspect of the invention there is provided a composition obtained as a result of the methods of the eighth (and/or related) or ninth (and/or related) broad aspects of the invention.

In an eleventh broad aspect of the invention there is provided a combination of two or more microorganisms acquired, selected or isolated by a method as herein before described.

In another aspect, the invention provides the use of one or more composition and/or microorganism acquired, selected or isolated by a method of the invention for imparting one or more beneficial property to one or more plant.

It should be appreciated that methods of the invention may also involve applying steps a) to c) (first aspect) or steps a) to d) (second and/or related aspect) of a method of the invention to two or more different species of plant so as to identify combinations of microorganisms that may impart a positive benefit to one species and a negative benefit to another species simultaneously. For example, one may wish to identify a group of microorganisms that may simultaneously improve the growth and survival of a food crop and suppress or inhibit the growth of a competing crop or weed. This may be achieved by using two or more different plant species in step a) or running separate methods on different species and at appropriate points combining the microorganisms acquired in those methods and conducting further iterations.

The invention also provides plants selected in a method of the invention.

The invention also provides the use of a method of the invention in a plant breeding programme, and a plant breeding programme comprising conducting a method of the invention.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

FIGURES

Figure 2:
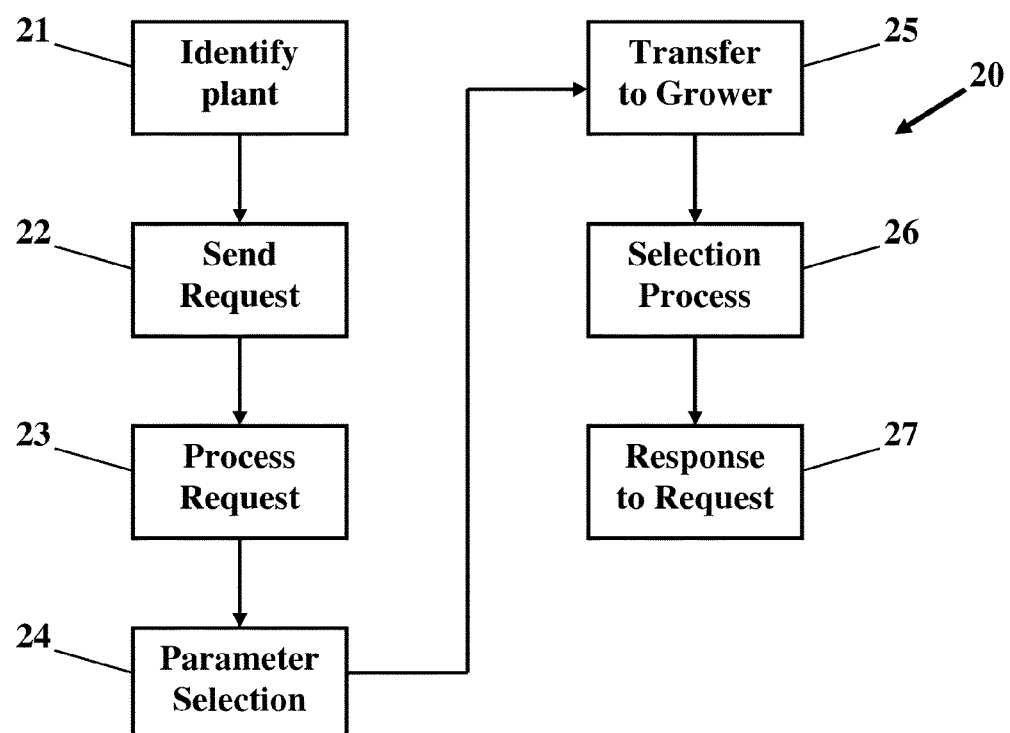

These and other aspects of the present invention, which should be considered in all its novel aspects, will become apparent from the following description, which is given by way of example only, with reference to the accompanying figures, in which:

FIG. 1: shows a system according to an embodiment of the invention;

FIG. 2: shows the process flow of a method of an embodiment of the invention.

PREFERRED EMBODIMENT(S)

The following is a description of the preferred forms of the present invention given in general terms. The invention will be further elucidated from the Examples provided hereafter.

The inventor(s) have found that one can readily identify microorganisms capable of imparting one or more beneficial property to one or more plants through use of a method of the invention. The method is broadly based on the presence of variability (such as genetic variability, or variability in the phenotype, for example) in the plants and microbial populations used. The inventors have identified that this variability can be used to support a directed process of selection of one or more microorganisms of use to a plant and for identifying particular plant/microbe combinations which are of benefit for a particular purpose, and which may never have been recognised using conventional techniques.

The methods of the invention may be used as a part of a plant breeding programme. The methods may allow for, or at least assist with, the selection of plants which have a particular genotype/phenotype which is influenced by the microbial flora, in addition to identifying microorganisms and/or compositions that are capable of imparting one or more property to one or more plants.

In one aspect the invention relates to a method for the selection of one or more microorganism(s) which are capable of imparting one or more beneficial property to a plant. It should be appreciated that as referred to herein a "beneficial property to a plant" should be interpreted broadly to mean any property which is beneficial for any particular purpose including properties which may be beneficial to human beings, other animals, the environment, a habitat, an ecosystem, the economy, of commercial benefit, or of any other benefit to any entity or system. Accordingly, the term should be taken to include properties which may suppress, decrease or block one or more characteristic of a plant, including suppressing, decreasing or inhibiting the growth or growth rate of a plant. The invention may be described herein, by way of example only, in terms of identifying positive benefits to one or more plants or improving plants. However, it should be appreciated that the invention is equally applicable to identifying negative benefits that can be conferred to plants.

Such beneficial properties include, but are not limited to, for example: improved growth, health and/or survival characteristics, resistance to pests and/or diseases, tolerance to growth in different geographical locations and/or different environmental biological and/or physical conditions, suitability or quality of a plant for a particular purpose, structure, colour, chemical composition or profile, taste, smell, improved quality. By way of example, the invention may allow for the identification of microorganisms which allow a plant to grow in a variety of different temperatures (including extreme temperatures), pH, salt concentrations, mineral concentrations, in the presence of toxins, and/or to respond to a greater extent to the presence of organic and/or inorganic fertilisers. In other embodiments, beneficial properties include, but are not limited to, for example; decreasing, suppressing or inhibiting the growth of a plant identified to be a weed; constraining the height and width of a plant to a desirable ornamental size; limiting the height of plants used in ground cover applications such as motorway and roadside banks and erosion control projects; slowing the growth of plants used in turf applications such as lawns, bowling greens and golf courses to reduce the necessity of mowing; reducing ratio of foliage/flowers in ornamental flowering shrubs; regulate production of and/or response to plant pheromones (resulting in increased tannin production in surrounding plant community and decreased appeal to foraging species).

As used herein, "improved" should be taken broadly to encompass improvement of a characteristic of a plant which may already exist in a plant or plants prior to application of the invention, or the presence of a characteristic which did not exist in a plant or plants prior to application of the invention. By way of example, "improved" growth should be taken to include growth of a plant where the plant was not previously known to grow under the relevant conditions.

As used herein, "inhibiting and suppressing" and like terms should be taken broadly and should not be construed to require complete inhibition or suppression, although this may be desired in some embodiments.

To assist in describing the invention, the terms a "first set of one or more microorganisms" and a "second set of one or more microorganisms" may be used herein to distinguish the set or group of microorganism(s) applied in step a) and the set or group of microorganism(s) (for example in step c) of the first aspect or in step d) of the second and/or related aspect) acquired in a method of the invention. In certain embodiments, the sets of microorganisms will be distinct; for example, the second set may be a subset of the first set, as a result of combining the first set with the plant and then selecting one or more plant based on one or more selection criterion. However, it should be appreciated that this may not always be the case and accordingly, the use of this terminology should not be construed in such a limited manner.

In certain embodiments, methods of the invention relate to selecting one or more microorganisms which are capable of imparting one or more beneficial property to a plant. As is further described herein after, such microorganism(s) may be contained within a plant, on a plant, and/or within the plant rhizosphere. Accordingly, where reference is made herein to acquiring a second set of one or more microorganisms "from" a plant, unless the context requires otherwise, it should be taken to include reference to acquiring a second set of microorganisms contained within a plant, on a plant and/or within the plant rhizosphere. For ease of reference, the wording "associated with" may be used synonymously to refer to microorganism(s) contained within a plant, on a plant and/or within the plant rhizosphere.

In one aspect, a method of the invention broadly comprises at least the steps of a) growing one or more plant in a growth medium in the presence of a first set of one or more microorganisms; b) selecting one or more plant following step a); and, c) acquiring a second set of one or more microorganisms associated with said one or more plant selected in step b). The one or more plants, growth medium and one or more microorganisms may be provided separately and combined in any appropriate order prior to step a). In particular, the invention provides an iterative method in which steps a) to c) may be repeated one or more times, wherein the one or more microorganisms acquired in step c) are used in step a) of a subsequent run or cycle of the method. In one embodiment, steps a) to c) are repeated once. In another embodiment, steps a) to c) are repeated twice. In another embodiment, steps a) to c) are repeated three times. In another embodiment, steps a) to c) are repeated at least until a desired beneficial property is observed.

In another aspect, the invention comprises a step of applying a selective pressure. Broadly, this method comprises at least the steps of a) growing one or more plant in a growth medium in the presence of one or more microorganisms; b) applying one or more selective pressure during step a); c) selecting one or more plant following step b); and, d) acquiring one or more microorganisms associated with said one or more plant selected in step c). The one or more plants, growth medium and one or more microorganisms may be provided separately and combined in any appropriate order prior to step a). In particular, the invention provides an iterative method in which steps a) to d) may be repeated one or more times, wherein the one or more microorganisms acquired in step d) are used in step a) of the next cycle of the method. In one embodiment, steps a) to d) are repeated once. In another embodiment, steps a) to d) are repeated twice. In another embodiment, steps a) to d) are repeated three times. In another embodiment, steps a) to d) are repeated at least at least until a desired beneficial property is observed. Whilst the same selective pressure(s) may be applied in each iteration of the method, different selective pressures may be applied in each iteration. In addition, the method may comprise a further step (or steps) which are conducted prior to step a) and include subjecting the one or more plant to a growth medium in the presence of one or more microorganisms but without a selective pressure. After a desired period, one or more microorganisms may be acquired from said one or more plant and can be used in step a) of the process. It should also be appreciated that successive rounds of this step may be conducted, with the microorganisms acquired being used in the subsequent round of the process, before embarking on steps a) to d) as described above. Further, the inventors envisage an iterative method in which steps a) to d) are repeated one or more times, but interspersed with the step of subjecting the plants to a growth medium and one or more microorganisms and isolating the microorganisms, without applying a selective pressure.

The methods of the invention include the steps of subjecting the first and/or second set of one or more microorganisms to a conditioning and/or directed evolution process prior to using these microorganisms in step a) of a process of the invention. The methods also envisage subjecting the second set of one or more microorganisms acquired at the end of the method to a conditioning and/or directed evolution process. The conditioning and directed evolution processes are described in more detail hereinafter.

It will be appreciated that after a desired number of repeats of steps a) to c) of a method of the first aspect of the invention or steps a) to d) of a method of the second and/or related aspect of the invention, or any combination thereof, the method may conclude with the acquisition of a set of one or more microorganisms from step c) or step d) (as the case may be) of any such method. In one embodiment, as noted above, after acquiring said set of one or more microorganisms, the method may further involve subjecting the set of one or more microorganisms to a conditioning and/or directed evolution process.

It should be appreciated that the methods do not require the identification of the microorganisms in the population acquired in the method (for example in step c) of the first aspect or step d) of the second and/or related aspect) nor do they require a determination of the beneficial properties of individual microorganisms or combinations of microorganisms acquired. However, evaluation, identification and/or a determination of the beneficial properties could be conducted if desired. For example, it may be preferred in some cases to isolate and identify the microbes in the final step of a method of the invention to determine their safety for commercial use and to satisfy regulatory requirements. In such cases, genetic and/or phenotypic analyses may be conducted.

In one embodiment of methods of the invention, step a) is conducted using at least two plants. In other embodiments 10 to 20 plants are used. In yet other embodiments, 20 or more, 50 or more, 100 or more, 300 or more, 500 or more or 1000 or more plants are used. As noted herein before, where two or more plants are used in a particular method of the invention they need not be the same variety or species. For example, in one embodiment it may be desirable to select microorganisms that can impart a positive benefit to one plant variety or species and a negative benefit to another plant variety or species.

In one embodiment, where two or more microorganisms are acquired (for example in step c) of the first aspect or in step d) of the second and/or related aspect), the method may further comprise the steps of separating the two or more microorganisms into individual isolates, selecting two or more individual isolates, and then combining the selected two or more isolates. This may result in the set of microorganisms acquired at the conclusion of a method of the invention. However, in one embodiment, the combined isolates may then be used in step a) of successive rounds of the method. By way of example, from two, three, four, five, six, seven, eight, nine or ten individual isolates may be combined. The inventors envisage an iterative method in which steps a) to d) (second and/or related aspect) or steps a) to c) (first aspect) are repeated one or more times, utilising these additional steps of separating, selecting and combining with each repeat of the method, or interspersed or otherwise combined with a method in which individual isolates are not selected and combined.

It is expected that these combinations will detect previously unknown synergistic interactions between acquired microbes that promote properties, such as plant growth. Application of the iterative steps of the methods will drive the starting population of two or more microorganisms toward microbes that interact with the plant to impart a desired property or characteristic. In other words, the process will allow for enrichment of suitable microorganisms within the plant microbiome.

Selection of individual isolates may occur on the basis of any appropriate selection criteria. For example, it may be random, it may be based on the beneficial property or properties observed by performing a method of the invention or, where information about the identity of the microorganism is known, it may be on the basis that the microorganism has previously been recognised to have a particular beneficial property.

In addition, two or more methods of the invention may be performed separately or in parallel and the microorganisms that result from each method combined into a single composition. For example, two separate methods may be performed, one to identify microorganisms capable of imparting one or more first beneficial property, and a second to identify microorganisms capable of imparting one or more second beneficial property. The separate methods may be directed to identifying microorganisms having the same beneficial property or having distinct beneficial properties. Where a method employing a selective pressure is used, the selective pressure in the separate methods may be the same or different. Similarly, the microorganisms and plants used in the separate methods may be the same or different. If further optimisation of the microorganisms is desired, the single composition of microorganisms may be applied to one or more further rounds of a method of the invention. Alternatively, the single composition of microorganisms may be used, as desired, to confer the relevant properties to plant crops, without further optimisation. Combining two or more methods of the invention in this way allows for the selection and combination of microorganisms which may ordinarily be separated by time and/or space in a particular environment.

In certain embodiments of the invention, the methods may comprise growing or propagating one or more plants selected in step c) (first aspect) or step d) (second and/or related aspect), to grow the population of the second set of one or more microorganisms associated with the selected one or more plants, either at the conclusion of a method of the invention, or prior to using the second set of one or more microorganisms in step a) of any successive repeat of the method. If the one or more plants (with associated microorganisms) are grown or propagated at the conclusion of a method of the invention they may then be used or sold in that form. Alternatively, one or more microorganisms may be isolated from the one or more plants, or one or more plant tissue and/or one or more plant part with associated microorganisms may be used as a crude source of the one or more microorganisms in any successive repeat of the invention, or for any other purpose at the conclusion of the method. In one embodiment, the seeds (with associated microorganisms) of one or more plant that has been grown or propagated may be obtained and used as a source of the one or more microorganisms in any successive repeat of the method. Alternatively, if obtained at the conclusion of a method of the invention, the seeds and associated microorganisms may be sold or used for any other purpose.

Further methods and aspects of the invention are described herein after.

Microorganisms

As used herein the term "microorganism" should be taken broadly. It includes but is not limited to the two prokaryotic domains, Bacteria and Archaea, as well as eukaryotic fungi and protists. By way of example, the microorganisms may include Proteobacteria (such as *Pseudomonas, Enterobacter, Stenotrophomonas, Burkholderia, Rhizobium, Herbaspirillum, Pantoea, Serratia, Rahnella, Azospirillum, Azorhizobium, Azotobacter, Duganella, Delftia, Bradyrhizobiun, Sinorhizobium* and *Halomonas*), Firmicutes (such as *Bacillus, Paenibacillus, Lactobacillus, Mycoplasma,* and *Acetobacterium*), Actinobacteria (such as *Streptomyces, Rhodococcus, Microbacterium,* and *Curtobacterium*), and the fungi Ascomycota (such as *Trichoderma, Ampelomyces,*

*Coniothyrium, Paecoelomyces, Penicillium, Cladosporium, Hypocrea, Beauveria, Metarhizium, Verticullium, Cordyceps, Pichea,* and *Candida,* Basidiomycota (such as *Coprinus, Corticium,* and *Agaricus*) and Oomycota (such as *Pythium, Mucor,* and *Mortierella*).

In a particularly preferred embodiment, the microorganism is an endophyte or an epiphyte or a microorganism inhabiting the plant rhizosphere. In one embodiment, the microorganism is a seed-borne endophyte.

In certain embodiments, the microorganism is unculturable. This should be taken to mean that the microorganism is not known to be culturable or is difficult to culture using methods known to one skilled in the art.

Microorganisms of use in the methods of the present invention (for example, as the first set of one or more microorganisms) may be collected or obtained from any source or contained within and/or associated with material collected from any source.

In one embodiment, the first set of one or more microorganisms are obtained from any general terrestrial environment, including its soils, plants, fungi, animals (including invertebrates) and other biota, including the sediments, water and biota of lakes and rivers; from the marine environment, its biota and sediments (for example sea water, marine muds, marine plants, marine invertebrates (for example sponges), marine vertebrates (for example, fish)); the terrestrial and marine geosphere (regolith and rock, for example crushed subterranean rocks, sand and clays); the cryo sphere and its meltwater; the atmosphere (for example, filtered aerial dusts, cloud and rain droplets); urban, industrial and other man-made environments (for example, accumulated organic and mineral matter on concrete, roadside gutters, roof surfaces, road surfaces).

In another embodiment the first set of one or more microorganisms are collected from a source likely to favour the selection of appropriate microorganisms. By way of example, the source may be a particular environment in which it is desirable for other plants to grow, or which is thought to be associated with terroir. In another example, the source may be a plant having one or more desirable traits, for example a plant which naturally grows in a particular environment or under certain conditions of interest. By way of example, a certain plant may naturally grow in sandy soil or sand of high salinity, or under extreme temperatures, or with little water, or it may be resistant to certain pests or disease present in the environment, and it may be desirable for a commercial crop to be grown in such conditions, particularly if they are, for example, the only conditions available in a particular geographic location. By way of further example, the microorganisms may be collected from commercial crops grown in such environments, or more specifically from individual crop plants best displaying a trait of interest amongst a crop grown in any specific environment, for example the fastest-growing plants amongst a crop grown in saline-limiting soils, or the least damaged plants in crops exposed to severe insect damage or disease epidemic, or plants having desired quantities of certain metabolites and other compounds, including fibre content, oil content, and the like, or plants displaying desirable colours, taste or smell. The microorganisms may be collected from a plant of interest or any material occurring in the environment of interest, including fungi and other animal and plant biota, soil, water, sediments, and other elements of the environment as referred to previously.

In certain embodiments, the microorganisms are sourced from previously performed methods of the invention (for example, the microorganisms acquired in step d) (second aspect) or step c) (first aspect) of the method), including combinations of individual isolates separated from the second set of microorganisms acquired in step c) (first aspect) or step d) (second and/or related aspect) or combinations of microorganisms resulting from two or more separately performed methods of the invention.

While the invention obviates the need for pre-existing knowledge about a microorganism's desirable properties with respect to a particular plant species, in one embodiment a microorganism or a combination of microorganisms of use in the methods of the invention may be selected from a pre-existing collection of individual microbial species or strains based on some knowledge of their likely or predicted benefit to a plant. For example, the microorganism may be predicted to: improve nitrogen fixation; release phosphate from the soil organic matter; release phosphate from the inorganic forms of phosphate (e.g. rock phosphate); "fix carbon" in the root microsphere; live in the rhizosphere of the plant thereby assisting the plant in absorbing nutrients from the surrounding soil and then providing these more readily to the plant; increase the number of nodules on the plant roots and thereby increase the number of symbiotic nitrogen fixing bacteria (e.g. *Rhizobium* species) per plant and the amount of nitrogen fixed by the plant; elicit plant defensive responses such as ISR (induced systemic resistance) or SAR (systemic acquired resistance) which help the plant resist the invasion and spread of pathogenic microorganisms; compete with microorganisms deleterious to plant growth or health by antagonism, or competitive utilisation of resources such as nutrients or space; change the colour of one or more part of the plant, or change the chemical profile of the plant, its smell, taste or one or more other quality.

In one embodiment a microorganism or combination of microorganisms (the first set of one or more microorganisms) is selected from a pre-existing collection of individual microbial species or strains that provides no knowledge of their likely or predicted benefit to a plant. For example, a collection of unidentified microorganisms isolated from plant tissues without any knowledge of their ability to improve plant growth or health, or a collection of microorganisms collected to explore their potential for producing compounds that could lead to the development of pharmaceutical drugs.

In one embodiment, the microorganisms are isolated from the source material (for example, soil, rock, water, air, dust, plant or other organism) in which they naturally reside. The microorganisms may be provided in any appropriate form, having regard to its intended use in the methods of the invention. However, by way of example only, the microorganisms may be provided as an aqueous suspension, gel, homogenate, granule, powder, slurry, live organism or dried material. The microorganisms may be isolated in substantially pure or mixed cultures. They may be concentrated, diluted or provided in the natural concentrations in which they are found in the source material. For example, microorganisms from saline sediments may be isolated for use in this invention by suspending the sediment in fresh water and allowing the sediment to fall to the bottom. The water containing the bulk of the microorganisms may be removed by decantation after a suitable period of settling and either applied directly to the plant growth medium, or concentrated by filtering or centrifugation, diluted to an appropriate concentration and applied to the plant growth medium with the bulk of the salt removed. By way of further example, microorganisms from mineralized or toxic sources may be similarly treated to recover the microbes for application to the plant growth material to minimise the potential for damage to the plant.

In another embodiment, the microorganisms (including the first set of one or more microorganisms and/or the second set of one or more microorganisms) are used in a crude form, in which they are not isolated from the source material in which they naturally reside. For example, the microorganisms are provided in combination with the source material in which they reside; for example, as soil, or the roots, seed or foliage of a plant. In this embodiment, the source material may include one or more species of microorganisms.

It is preferred that a mixed population of microorganisms is used in the methods of the invention.

In embodiments of the invention where the microorganisms are isolated from a source material (for example, the material in which they naturally reside), any one or a combination of a number of standard techniques which will be readily known to skilled persons may be used. However, by way of example, these in general employ processes by which a solid or liquid culture of a single microorganism can be obtained in a substantially pure form, usually by physical separation on the surface of a solid microbial growth medium or by volumetric dilutive isolation into a liquid microbial growth medium. These processes may include isolation from dry material, liquid suspension, slurries or homogenates in which the material is spread in a thin layer over an appropriate solid gel growth medium, or serial dilutions of the material made into a sterile medium and inoculated into liquid or solid culture media.

Whilst not essential, in one embodiment, the material containing the microorganisms may be pre-treated prior to the isolation process in order to either multiply all microorganisms in the material, or select portions of the microbial population, either by enriching the material with microbial nutrients (for example, nitrates, sugars, or vegetable, microbial or animal extracts), or by applying a means of ensuring the selective survival of only a portion of the microbial diversity within the material (for example, by pasteurising the sample at 60° C.-80° C. for 10-20 minutes to select for microorganisms resistant to heat exposure (for example, bacilli), or by exposing the sample to low concentrations of an organic solvent or sterilant (for example, 25% ethanol for 10 minutes) to enhance the survival of actinomycetes and spore-forming or solvent-resistant microorganisms). Microorganisms can then be isolated from the enriched materials or materials treated for selective survival, as above.

In a preferred embodiment of the invention endophytic or epiphytic microorganisms are isolated from plant material. Any number of standard techniques known in the art may be used and the microorganisms may be isolated from any appropriate tissue in the plant, including for example root, stem and leaves, and plant reproductive tissues. By way of example, conventional methods for isolation from plants typically include the sterile excision of the plant material of interest (e.g. root or stem lengths, leaves), surface sterilisation with an appropriate solution (e.g. 2% sodium hypochlorite), after which the plant material is placed on nutrient medium for microbial growth (see, for example, Strobel G and Daisy B (2003) Bioprospecting for microbial endophytes and their natural products. Microbiology and Molecular Biology Reviews 67 (4): 491-502; Zinniel D K et al. (2002) Isolation and characterisation of endophytic colonising bacteria from agronomic crops and prairie plants. Applied and Environmental Microbiology 68 (5): 2198-2208. In one preferred embodiment of the invention, the microorganisms are isolated from root tissue. Further methodology for isolating microorganisms from plant material are detailed herein after.

As used herein, "isolate", "isolated" and like terms should be taken broadly. These terms are intended to mean that the one or more microorganism(s) has been separated at least partially from at least one of the materials with which it is associated in a particular environment (for example soil, water, plant tissue). "Isolate", "isolated" and like terms should not be taken to indicate the extent to which the microorganism(s) has been purified.

As used herein, "individual isolates" should be taken to mean a composition or culture comprising a predominance of a single genera, species or strain of microorganism, following separation from one or more other microorganisms. The phrase should not be taken to indicate the extent to which the microorganism has been isolated or purified. However, "individual isolates" preferably comprise substantially only one genus, species or strain of microorganism.

In one embodiment, the microbial population is exposed (prior to the method or at any stage of the method) to a selective pressure to enhance the probability that the eventually-selected plants will have microbial assemblages likely to have desired properties. For example, exposure of the microorganisms to pasteurisation before their addition to a plant growth medium (preferably sterile) is likely to enhance the probability that the plants selected for a desired trait will be associated with spore-forming microbes that can more easily survive in adverse conditions, in commercial storage, or if applied to seed as a coating, in an adverse environment.

It should be appreciated that the second set of microorganisms acquired in a method of the invention may be isolated from a plant or plant material, surface or growth media associated with a selected plant using any appropriate techniques known in the art, including but not limited to those techniques described herein. However, in certain embodiments, as mentioned herein before, the microorganism(s) may be used in crude form and need not be isolated from a plant or a media. For example, plant material or growth media which includes the microorganisms identified to be of benefit to a selected plant may be obtained and used as a crude source of microorganisms for the next round of the method or as a crude source of microorganisms at the conclusion of the method. For example, whole plant material could be obtained and optionally processed, such as mulched or crushed. Alternatively, individual tissues or parts of selected plants (such as leaves, stems, roots, seeds) may be separated from the plant and optionally processed, such as mulched or crushed. In certain embodiments, one or more part of a plant which is associated with the second set of one or more microorganisms may be removed from one or more selected plants and, where any successive repeat of the method is to be conducted, grafted on to one or more plant used in step a).

The methods of the invention may be described herein in terms of the second set of one or more microorganisms being isolated from its source material. However, unless the context requires otherwise, this should also be taken to include reference to the use of microorganisms in crude form in which they have not been isolated from the source material.

Plants

Any number of a variety of different plants, including mosses and lichens and algae, may be used in the methods of the invention. In preferred embodiments, the plants have economic, social and/or environmental value. For example, the plants may include those of use: as food crops; as fibre crops; as oil crops; in the forestry industry; in the pulp and paper industry; as a feedstock for biofuel production; and/or, as ornamental plants. In other embodiments, the plants may be economically, socially and/or environmentally undesirable, such as weeds. The following is a list of non-limiting examples of the types of plants the methods of the invention may be applied to:

Food crops:
- Cereals (maize, rice, wheat, barley, sorghum, millet, oats, rye, triticale, buckwheat);
- leafy vegetables (brassicaceous plants such as cabbages, broccoli, bok choy, rocket; salad greens such as spinach, cress, lettuce);
- fruiting and flowering vegetables (e.g. avocado, sweet corn, artichokes, curcubits e.g. squash, cucumbers, melons, courgettes, pumpkins; solononaceous vegetables/fruits e.g. tomatoes, eggplant, capsicums);
- podded vegetables (groundnuts, peanuts, peas, soybeans, beans, lentils, chickpea, okra);
- bulbed and stem vegetables (asparagus, celery, *Allium* crops e.g garlic, onions, leeks);
- roots and tuberous vegetables (carrots, beet, bamboo shoots, cassava, yams, ginger, Jerusalem artichoke, parsnips, radishes, potatoes, sweet potatoes, taro, turnip, wasabi);
- sugar crops including sugar beet (*Beta vulgaris*), sugar cane (*Saccharum officinarum*);
- crops grown for the production of non-alcoholic beverages and stimulants (coffee, black, herbal and green teas, cocoa, tobacco);
- fruit crops such as true berry fruits (e.g. kiwifruit, grape, currants, gooseberry, guava, feijoa, pomegranate), citrus fruits (e.g. oranges, lemons, limes, grapefruit), epigynous fruits (e.g. bananas, cranberries, blueberries), aggregate fruit (blackberry, raspberry, boysenberry), multiple fruits (e.g. pineapple, fig), stone fruit crops (e.g. apricot, peach, cherry, plum), pip-fruit (e.g. apples, pears) and others such as strawberries, sunflower seeds;
- culinary and medicinal herbs e.g. rosemary, basil, bay laurel, coriander, mint, dill, *Hypericum*, foxglove, alovera, rosehips);
- crop plants producing spices e.g. black pepper, cumin cinnamon, nutmeg, ginger, cloves, saffron, cardamom, mace, paprika, masalas, star anise;
- crops grown for the production of nuts e.g. almonds and walnuts, Brazil nut, cashew nuts, coconuts, chestnut, macadamia nut, pistachio nuts; peanuts, pecan nuts;
- crops grown for production of beers, wines and other alcoholic beverages e.g grapes, hops;
- oilseed crops e.g. soybean, peanuts, cotton, olives, sunflower, sesame, lupin species and brassicaeous crops (e.g. canola/oilseed rape); and,
- edible fungi e.g. white mushrooms, Shiitake and oyster mushrooms;

Plants Used in Pastoral Agriculture:
- legumes: *Trifolium* species, *Medicago* species, and *Lotus* species; White clover (*T. repens*); Red clover (*T. pratense*); Caucasian clover (*T. ambigum*); subterranean clover (*T. subterraneum*); Alfalfa/Lucerne (*Medicago sativum*); annual medics; barrel medic; black medic; Sainfoin (*Onobrychis viciifolia*); Birdsfoot trefoil (*Lotus corniculatus*); Greater Birdsfoot trefoil (*Lotus pedunculatus*);
- seed legumes/pulses including Peas (*Pisum sativum*), Common bean (*Phaseolus vulgaris*), Broad beans (*Vicia faba*), Mung bean (*Vigna radiata*), Cowpea (*Vigna unguiculata*), Chick pea (*Cicer arietum*), Lupins (*Lupinus* species);
- Cereals including Maize/corn (*Zea mays*), Sorghum (*Sroghum* spp.), Millet (*Panicum miliaceum*, *P. sumatrense*), Rice (*Oryza sativa indica*, *Oryza sativa japonica*), Wheat (*Triticum sativa*), Barley (*Hordeum vulgare*), Rye (*Secale cereale*), Triticale (*Triticum× Secale*), Oats (*Avena fatua*);
- Forage and Amenity grasses: Temperate grasses such as *Lolium* species; *Festuca* species; *Agrostis* spp., Perennial ryegrass (*Lolium perenne*); hybrid ryegrass (*Lolium hybridum*); annual ryegrass (*Lolium multiflorum*), tall fescue (*Festuca arundinacea*); meadow fescue (*Festuca pratensis*); red fescue (*Festuca rubra*); *Festuca ovina*; Festuloliums (*Lolium×Festuca* crosses); Cocksfoot (*Dactylis glomerata*); Kentucky bluegrass *Poa pratensis; Poa palustris; Poa nemoralis; Poa trivialis; Poa compresa; Bromus* species; *Phalaris* (*Phleum* species); *Arrhenatherum elatius; Agropyron* species; *Avena strigosa; Setaria italic;*
- Tropical grasses such as: *Phalaris* species; *Brachiaria* species; *Eragrostis* species; *Panicum* species; Bahai grass (*Paspalum notatum*); *Brachypodium* species; and,
- Grasses used for biofuel production such as Switchgrass (*Panicum virgatum*) and *Miscanthus* species;

Fibre Crops:
- cotton, hemp, jute, coconut, sisal, flax (*Linum* spp.), New Zealand flax (*Phormium* spp.); plantation and natural forest species harvested for paper and engineered wood fibre products such as coniferous and broadleafed forest species;

Tree and Shrub Species Used in Plantation Forestry and Bio Fuel Crops:
- Pine (*Pinus* species); Fir (*Pseudotsuga* species); Spruce (*Picea* species); Cypress (*Cupressus* species); Wattle (*Acacia* species); Alder (*Alnus* species); Oak species (*Quercus* species); Redwood (*Sequoiadendron* species); willow (*Salix* species); birch (*Betula* species); Cedar (*Cedurus* species); Ash (*Fraxinus* species); Larch (*Larix* species); *Eucalyptus* species; Bamboo (*Bambuseae* species) and Poplars (*Populus* species).

Plants Grown for Conversion to Energy, Biofuels or Industrial Products by Extractive, Biological, Physical or Biochemical Treatment:
- Oil-producing plants such as oil palm, jatropha, soybean, cotton, linseed;
- Latex-producing plants such as the Para Rubber tree, *Hevea brasiliensis* and the Panama Rubber Tree *Castilla elastica;*
- plants used as direct or indirect feedstocks for the production of biofuels i.e. after chemical, physical (e.g. thermal or catalytic) or biochemical (e.g. enzymatic pre-treatment) or biological (e.g. microbial fermentation) transformation during the production of biofuels, industrial solvents or chemical products e.g. ethanol or butanol, propane diols, or other fuel or industrial material including sugar crops (e.g. beet, sugar cane), starch-producing crops (e.g. C3 and C4 cereal crops and tuberous crops), cellulosic crops such as forest trees (e.g. Pines, Eucalypts) and Graminaceous and Poaceous plants such as bamboo, switch grass, *miscanthus;*
- crops used in energy, biofuel or industrial chemical production via gasification and/or microbial or catalytic conversion of the gas to biofuels or other industrial raw materials such as solvents or plastics, with or without the production of biochar (e.g. biomass crops such as coniferous, eucalypt, tropical or broadleaf forest trees, graminaceous and poaceous crops such as bamboo, switch grass, *miscanthus*, sugar cane, or hemp or softwoods such as poplars, willows; and, biomass crops used in the production of biochar;

Crops Producing Natural Products Useful for the Pharmaceutical, Agricultural Nutraceutical and Cosmeceutical Industries:

crops producing pharmaceutical precursors or compounds or nutraceutical and cosmeceutical compounds and materials for example, star anise (shikimic acid), Japanese knotweed (resveratrol), kiwifruit (soluble fibre, proteolytic enzymes);

Floricultural, Ornamental and Amenity Plants Grown for their Aesthetic or Environmental Properties:

Flowers such as roses, tulips, chrysanthemums;

Ornamental shrubs such as *Buxus, Hebe, Rosa, Rhododendron, Hedera*

Amenity plants such as *Platanus, Choisya, Escallonia, Euphorbia, Carex*

Mosses such as sphagnum moss

Plants Grown for Bioremediation:

*Helianthus, Brassica, Salix, Populus, Eucalyptus*

It should be appreciated that a plant may be provided in the form of a seed, seedling, cutting, propagule, or any other plant material or tissue capable of growing. In one embodiment the seed may surface-sterilised with a material such as sodium hypochlorite or mercuric chloride to remove surface-contaminating microorganisms. In one embodiment, the propagule is grown in axenic culture before being placed in the plant growth medium, for example as sterile plantlets in tissue culture.

Growth Medium

The term "growth medium" as used herein, should be taken broadly to mean any medium which is suitable to support growth of a plant. By way of example, the media may be natural or artificial including, but not limited to, soil, potting mixes, bark, vermiculite, hydroponic solutions alone and applied to solid plant support systems, and tissue culture gels. It should be appreciated that the media may be used alone or in combination with one or more other media. It may also be used with or without the addition of exogenous nutrients and physical support systems for roots and foliage.

In one embodiment, the growth medium is a naturally occurring medium such as soil, sand, mud, clay, humus, regolith, rock, or water. In another embodiment, the growth medium is artificial. Such an artificial growth medium may be constructed to mimic the conditions of a naturally occurring medium, however, this is not necessary. Artificial growth media can be made from one or more of any number and combination of materials including sand, minerals, glass, rock, water, metals, salts, nutrients, water. In one embodiment, the growth medium is sterile. In another embodiment, the growth medium is not sterile.

The medium may be amended or enriched with additional compounds or components, for example, a component which may assist in the interaction and/or selection of specific groups of microorganisms with the plant and each other. For example, antibiotics (such as penicillin) or sterilants (for example, quaternary ammonium salts and oxidizing agents) could be present and/or the physical conditions (such as salinity, plant nutrients (for example organic and inorganic minerals (such as phosphorus, nitrogenous salts, ammonia, potassium and micronutrients such as cobalt and magnesium), pH, and/or temperature) could be amended.

In certain embodiments of the invention, the growth medium may be pre-treated to assist in the survival and/or selection of certain microorganisms. For example, the medium may be pre-treated by incubating in an enrichment media to encourage the multiplication of endogenous microbes that may be present therein. By way of further example, the medium may be pre-treated by incubating in a selective medium to encourage the multiplication of specific groups of microorganisms. A further example includes the growth medium being pre-treated to exclude a specific element of the microbial assemblage therein; for example pasteurization (to remove spore-forming bacteria and fungi) or treatment with organic solvents such as various alcohols to remove microorganisms sensitive to these materials but allow the survival of actinomycetes and spore-forming bacteria, for example.

Methods for pre-treating or enriching may be informed by culture independent microbial community profiling techniques that provide information on the identity of microbes or groups of microbes present. These methods may include, but are not limited to, sequencing techniques including high throughput sequencing and phylogenetic analysis, or microarray-based screening of nucleic acids coding for components of rRNA operons or other taxonomically informative loci.

Growth Conditions

In accordance with the methods of the invention one or more plant is subjected to one or more microorganism and a growth medium. The plant is preferably grown or allowed to multiply in the presence of the one or more microorganism(s) and growth medium. The microorganism(s) may be present in the growth medium naturally without the addition of further microorganisms, for example in a natural soil. The growth medium, plant and microorganisms may be combined or exposed to one another in any appropriate order. In one embodiment, the plant, seed, seedling, cutting, propagule or the like is planted or sown into the growth medium which has been previously inoculated with the one or more microorganisms. Alternatively, the one or more microorganisms may be applied to the plant, seed, seedling, cutting, propagule or the like which is then planted or sown into the growth medium (which may or may not contain further microorganisms). In another embodiment, the plant, seed, seedling, cutting, propagule or the like is first planted or sown into the growth medium, allowed to grow, and at a later time the one or more microorganisms are applied to the plant, seed, seedling, cutting, propagule or the like and/or the growth medium itself is inoculated with the one or more microorganisms.

The microorganisms may be applied to the plant, seedling, cutting, propagule or the like and/or the growth medium using any appropriate techniques known in the art. However, by way of example, in one embodiment, the one or more microorganisms are applied to the plant, seedling, cutting, propagule or the like by spraying or dusting. In another embodiment, the microorganisms are applied directly to seeds (for example as a coating) prior to sowing. In a further embodiment, the microorganisms or spores from microorganisms are formulated into granules and are applied alongside seeds during sowing. In another embodiment, microorganisms may be inoculated into a plant by cutting the roots or stems and exposing the plant surface to the microorganisms by spraying, dipping or otherwise applying a liquid microbial suspension, or gel, or powder. In another embodiment the microorganism(s) may be injected directly into foliar or root tissue, or otherwise inoculated directly into or onto a foliar or root cut, or else into an excised embryo, or radicle or coleoptile. These inoculated plants may then be further exposed to a growth media containing further microorganisms, however, this is not necessary. In certain embodiments, the microorganisms are applied to the plant, seedling, cutting, propagule or the like and/or growth medium in association with plant material (for example, plant material with which the microorganisms are associated).

In other embodiments, particularly where the microorganisms are unculturable, the microorganisms may be transferred to a plant by any one or a combination of grafting, insertion of explants, aspiration, electroporation, wounding, root pruning, induction of stomatal opening, or any physical, chemical or biological treatment that provides the opportunity for microbes to enter plant cells or the intercellular space. Persons of skill in the art may readily appreciate a number of alternative techniques that may be used.

It should be appreciated that such techniques are equally applicable to application of the first set of one or more microorganisms and the second set of microorganisms when used in step a) of a successive repeat of the method.

In one embodiment the microorganisms infiltrate parts of the plant such as the roots, stems, leaves and/or reproductive plant parts (become endophytic), and/or grow upon the surface of roots, stems, leaves and/or reproductive plant parts (become epiphytic) and/or grow in the plant rhizosphere. In one preferred embodiment microorganism(s) form a symbiotic relationship with the plant.

The growth conditions used may be varied depending on the species of plant, as will be appreciated by persons skilled in the art. However, by way of example, for clover, in a growth room one would typically grow plants in a soil containing approximately $\frac{1}{3}^{rd}$ organic matter in the form of peat, $\frac{1}{3}^{rd}$ compost, and $\frac{1}{3}^{rd}$ screened pumice, supplemented by fertilisers typically containing nitrates, phosphates, potassium and magnesium salts and micronutrients and at a pH of between 6 and 7. The plants may be grown at a temperature between 22-24° C. in an 16:8 period of daylight: darkness, and watered automatically.

Selective Pressure

In certain aspects and embodiments of the invention, at a desired time during the period within which the plant may be subjected to one or more microorganism and a growth medium, a selective pressure may be applied. The selective pressure may be any biotic or abiotic factor or element which may have an impact on the health, growth, and/or survival of a particular plant, including environmental conditions and elements which plants may be exposed to in their natural environment or a commercial situation.

Examples of biotic selective pressures include but are not limited to organisms that are detrimental to the plant, for example, fungi, bacteria, viruses, insects, mites, nematodes, animals.

Abiotic selective pressures include for example any chemical and physical factors in the environment; for example, water availability, soil mineral composition, salt, temperature, alterations in light spectrum (e.g. increased UV light), pH, organic and inorganic toxins (for example, exposure to or changes in the level of toxins), metals, organic nutrients, inorganic nutrients, air quality, atmospheric gas composition, air flow, rain fall, and hail.

For example, the plant/microorganisms may be exposed to a change in or extreme salt concentrations, temperature, pH, higher than normal levels of atmospheric gases such as $CO_2$, water levels (including drought conditions or flood conditions), low nitrogen levels, provision of phosphorus in a form only available to the plant after microbial degradation, exposure to or changes in the level of toxins in the environment, soils with nearly toxic levels of certain minerals such as aluminates, or high winds.

In one embodiment the selective pressure is applied directly to the plant, the microorganisms and/or the growth medium. In another embodiment the selective pressure is applied indirectly to the plant, the microorganisms and/or the growth medium, via the surrounding environment; for example, a gaseous toxin in the air or a flying insect.

The selective pressure may be applied at any time, preferably during the time the plant is subjected to the one or more microorganism and growth medium. In one embodiment, the selective pressure is applied during for substantially the whole time during which a plant is growing and/or multiplying. In another embodiment, the selective pressure is applied at a discrete time point during growth and/or multiplication. By way of example, the selective pressure may be applied at different growth phases of the one or more plants which simulate a potential stress on the plant that might occur in a natural or commercial setting. For example, the inventor has observed that some pests attack plants only at specific stages of the plant's life. In addition, the inventor has observed that different populations of potentially beneficial microorganisms can associate with plants at different points in the plant's life. Simulating a pest attack on the plant at the relevant time point, may allow for the identification and isolation of microorganisms which may protect the plant from attack at that particular life stage. It should also be appreciated that the selective pressure may be present in the growth medium or in the general environment at the time the plant, seed, seedling, cutting, propagule or the like is planted or sown.

In one embodiment, the microbial population is exposed (prior to the method or at any stage of the method) to a selective pressure to enhance the probability that the eventually-selected plants will have microbial assemblages likely to have desired properties. For example, exposure of the microorganisms to pasteurisation before their addition to a plant growth medium (preferably sterile) is likely to enhance the probability that the plants selected for a desired trait will be associated with spore-forming microbes that can more easily survive in adverse conditions, in commercial storage, or if applied to seed as a coating, in an adverse environment. Another example is provided herein after in Example 11B, in which microorganisms were subjected to a media which allowed for selection of phosphate solubilising microbes. Such a step of applying a selective pressure to the microbial population may be referred to herein as an "enrichment step".

The plants may be grown and subjected to the selective pressure for any appropriate length of time before they are selected and harvested. By way of example only, the plants and any microorganisms associated with them may be selected and harvested at any time during the growth period of a plant, in one embodiment, any time after germination of the plant. In a preferred embodiment, the plants are grown or allowed to multiply for a period which allows one to distinguish between plants having desirable phenotypic features and those that do not. By way of general example wheat may be selected for improvements in the speed of foliar growth say after one month, but equally may be selected for superior grain yield on maturity of the seed head. The length of time a plant is grown depends on the timing required to express the plant trait that is desired to be improved by the invention, or the time required to express a trait correlated with the desired trait. For example, in the case of winter wheat varieties, mainly sown in the Northern Hemisphere, it may be important to select plants that display early tillering after exposure of seed to a growth medium containing microorganisms under conditions of light and temperature similar to experienced by the winter wheat seed in the Northern Hemisphere, since early tillering is a trait related to winter survival, growth and eventual grain yield in the summer. Or, a tree species may be selected for improved growth and health at 4-6 months as these traits are related to the health and growth rate and size of trees of 10 years later, an impractical period for product development using this invention. It should be appreciated that the methods of the invention may involve applying two or more selective pressures simultaneously or successively in step b).

Selection

Typically, following growth of the one or more plants in the presence of one or more microorganisms, and in certain embodiments following exposure to a selective pressure, one or more plant is selected based on one or more selection criterion. In one embodiment the plants are selected on the basis of one or more phenotypic traits. Skilled persons will readily appreciate that such traits include any observable characteristic of the plant, including for example growth rate, height, weight, colour, taste, smell, changes in the production of one or more compounds by the plant (including for example, metabolites, proteins, drugs, carbohydrates, oils, and any other compounds). Selecting plants based on genotypic information is also envisaged (for example, including the pattern of plant gene expression in response to the microorganisms, genotype, presence of genetic markers). It should be appreciated that in certain embodiments, plants may be selected based on the absence, suppression or inhibition of a certain feature or trait (such as an undesirable feature or trait) as opposed to the presence of a certain feature or trait (such as a desirable feature or trait).

Where the presence of one or more genetic marker is assessed, the one or more marker may already be known and/or associated with a particular characteristic of a plant; for example, a marker or markers associated with an increased growth rate or metabolite profile. This information could be used in combination with assessment based on other characteristics in a method of the invention to select for a combination of different plant characteristics that may be desirable. Such techniques may be used to identify novel QTLs which link desirable plant traits with a specific microbial flora—for example matching plant genotype to the microbiome type.

By way of example, plants may be selected based on growth rate, size (including but not limited to weight, height, leaf size, stem size, branching pattern, or the size of any part of the plant), general health, survival, tolerance to adverse physical environments and/or any other characteristic, as described herein before. Further non-limiting examples include selecting plants based on: speed of seed germination; quantity of biomass produced; increased root, and/or leaf/shoot growth that leads to an increased yield (herbage or grain or fibre or oil) or biomass production; effects on plant growth that results in an increased seed yield for a crop, which may be particularly relevant in cereal crops such as wheat, barley, oats, rye, maize, rice, sorghum, oilseed crops such as soybean, canola, cotton, sunflower, and seed legumes such as peas, beans; effects on plant growth that result in an increased oil yield, which may be particularly relevant in oil seed crops such as soybean, canola, cotton, jatropha and sunflower; effects on plant growth that result in an increased fibre yield (e.g. in cotton, flax and linseed) or for effects that result in an increased tuber yield in crops such as potatoes and sugar beet; effects on plant growth that result in an increased digestibility of the biomass which may be particularly relevant in forage crops such as forage legumes (alfalfa, clovers, medics), forage grasses (*Lolium* species; *Festuca* species; *Paspalum* species; *Brachiaria* species; *Eragrostis* species), forage crops grown for silage such as maize and forage cereals (wheat, barley, oats); effects on plant growth which result in an increased fruit yield which may be particularly relevant to pip fruit trees (such as apples, pears, etc), berry fruits (such as strawberries, raspberries, cranberries), stone fruit (such as nectarines, apricots), and citrus fruit, grapes, figs, nut trees; effects on plant growth that lead to an increased resistance or tolerance disease including fungal, viral or bacterial diseases or to pests such as insects, mites or nematodes in which damage is measured by decreased foliar symptoms such as the incidence of bacterial or fungal lesions, or area of damaged foliage or reduction in the numbers of nematode cysts or galls on plant roots, or improvements in plant yield in the presence of such plant pests and diseases; effects on plant growth that lead to increased metabolite yields, for example in plants grown for pharmaceutical, nutraceutical or cosmeceutical purposes which may be particularly relevant for plants such as star anise grown for the production of shikimic acid critical for the production of anti-influenza drug oseltamivir, or the production of Japanese knotweed for the extraction of resveratrol, or the production of soluble fibre and dietary enzyme products from kiwifruit, or for example increased yields of "condensed tannins" or other metabolites useful for inhibiting the production of greenhouse gases such as methane in grazing animals; effects on plant growth that lead to improved aesthetic appeal which may be particularly important in plants grown for their form, colour or taste, for example the colour intensity and form of ornamental flowers, the taste of fruit or vegetable, or the taste of wine from grapevines treated with microorganisms; and, effects on plant growth that lead to improved concentrations of toxic compounds taken up or detoxified by plants grown for the purposes of bioremediation. Selection of plants based on phenotypic or genotypic information may be performed using techniques such as, but not limited to: high through-put screening of chemical components of plant origin, sequencing techniques including high through-put sequencing of genetic material, differential display techniques (including DDRT-PCR, and DD-PCR), nucleic acid microarray techniques, RNA-seq (Whole Transcriptome Shotgun Sequencing), qRT-PCR (quantitative real time PCR).

In certain embodiments of the invention, selection for a combination of plant traits may be desired; for example, in the embodiments of the invention which involve repeating the basic method steps and applying different selective pressures with each iteration of the method. This can be achieved in a number of ways. In one embodiment, multiple rounds of iterative improvement for one trait, e.g. superior growth in nematode infested soils, are maintained until an acceptable level of nematode resistance is attained. Similar, but completely separate rounds of selection are undertaken to identify microorganisms that can confer at least different desirable traits, for example simply for improved growth or other characteristics, or improved growth resulting from improved microbial soil phosphate utilisation, or improved growth resulting from increased tolerance to sucking insect pests. Such separate rounds of selection may be performed using an iterative or stacking approach or a combination of separate methods could be used, with the microorganisms that result from those separate rounds or methods being combined into a single composition. At this point the microorganism(s) could be developed into a product containing combinations of separately-fermented microorganisms each shown to improve a different plant attribute. In a further embodiment, the separately selected sets of microorganisms may be combined in sets of two or more and used in further methods of the invention. In another embodiment, the separately selected sets of microorganisms may be separated into individual isolates and then individual isolates combined in sets of two or more and used in further methods of the invention. In one embodiment, the combined microorganisms are applied to the plant and/or growth medium for the application of two or more selection pressures in the same iterative cycle. For example, in one combination, microorganisms able to improve plant growth in a medium containing low-levels of plant-available phosphorus are combined with microorganisms able to enhance plant growth in soils infested with plant parasitic nematodes. The combined microorganisms are then added to a plant growth medium with low levels of available phosphorus in which the plants are grown for a suitable period, nematodes applied and the plants are further grown until nematode damage can be expressed. The degree of nematode root damage and plant biomass is assessed non-destructively and microbes are isolated from the best-performing plants for use in a succeeding iteration. Similar iterative rounds may be continued until an acceptable level of plant growth is attained under both selective pressures. This approach will aid the selection of microbes that synergistically improve plant performance i.e. improve plant growth and nematode resistance to a degree better than that achieved if the microorganisms are applied simply as a combination of two separately-selected sets. The same approach could be used in methods of the invention which do not employ the application of one or more selective pressure. For example, the microorganisms acquired from separate runs of a method of the invention, each shown to be associated with different desirable plant characteristics (by way of non-limiting example, sugar or fibre content and growth rate, or flower colour and height) could be combined into a single composition and applied to one or more plants in a further round of the method for selection of plants having both characteristics or yet a further characteristic.

Harvesting

Following selection, one or more plants are harvested and plant tissues may be examined to detect microorganisms forming associations with the plants (for example, endophytic, epiphytic or rhizospheric associations).

The techniques described in this section may be used in acquiring a second set of microorganisms at the conclusion of a method of the invention or for use in any successive repeat of the methods of the invention.

The one or more microorganisms may be isolated from any appropriate tissue of the plants selected; for example, whole plant, foliar tissue, stem tissue, root tissue, and/or seeds. In a preferred embodiment, the microorganisms are isolated from the root tissue, stem or foliar tissues and/or seeds of the one or more plants selected.

In certain embodiments, the microorganisms may be acquired in crude form, in which they are not isolated from the source material in which they reside (such as a plant, plant tissue or part or growth media).

Where isolation of the microorganisms occurs, they may be isolated from the plants using any appropriate methods known in the art. However, by way of example, methods for isolating endophytic microbes may include the sterile excision of the plant material of interest (e.g. root, stem lengths, seed), surface sterilisation with an appropriate solution (e.g. 2% sodium hypochlorite), after which the plant material is placed on nutrient medium for microbial outgrowth, especially filamentous fungi. Alternatively, the surface-sterilised plant material can be crushed in a sterile liquid (usually water) and the liquid suspension, including small pieces of the crushed plant material spread over the surface of a suitable solid agar medium, or media, which may or may not be selective (e.g. contain only phytic acid as a source of phosphorus). This approach is especially useful for bacteria and yeasts which form isolated colonies and can be picked off individually to separate plates of nutrient medium, and further purified to a single species by well-known methods. Alternatively, the plant root or foliage samples may not be surface sterilised but only washed gently thus including surface-dwelling epiphytic microorganisms in the isolation process, or the epiphytic microbes can be isolated separately, by imprinting and lifting off pieces of plant roots, stem of leaves on to the surface of an agar medium and then isolating individual colonies as above. This approach is especially useful for bacteria and yeasts, for example. Alternatively, the roots may be processed without washing off small quantities of soil attached to the roots, thus including microbes that colonise the plant rhizosphere. Otherwise, soil adhering to the roots can be removed, diluted and spread out onto agar of suitable selective and non-selective media to isolate individual colonies of rhizospheric microbes. Further exemplary methodology can be found in: Strobel G and Daisy B (2003) Bioprospecting for microbial endophytes and their natural products. Microbiology and Molecular Biology Reviews 67 (4): 491-502; Zinniel D K et al. (2002) Isolation and characterisation of endophytic colonising bacteria from agronomic crops and prairie plants. Applied and Environmental Microbiology 68 (5): 2198-2208; Manual of Environmental Microbiology, Hurst et al., ASM Press, Washington D.C.

Methods for isolation may be informed by culture independent community profiling techniques that provide information on the identity and activity of microbes present in a given sample. These methods may include, but are not limited to, sequencing techniques including high throughput sequencing and phylogenetic analysis, or microarray-based screening of nucleic acids coding for components of rRNA operons or other taxonomically informative loci.

In embodiments of the invention where two or more microorganism are isolated from plant material and then separated into individual isolates, any appropriate methodology for separating one or more microorganism from each other may be used. However, by way of example, microbial extracts prepared from plant material could be spread on agar plates, grown at an appropriate temperature for a suitable period of time and the resulting microbial colonies subsequently selected and grown in an appropriate media (for example, streaked onto fresh plates or grown in a liquid medium). The colonies may be selected based on morphology or any other appropriate selection criteria as will be understood in the art. By way of further example, selective media could be used.

The one or more microorganisms may be harvested (including in isolated or crude form) from the plants (including the rhizosphere as described herein before) at any appropriate time point. In one embodiment they are harvested at any time after germination of the plant. For example, they can be isolated from the period shortly after germination (where survival in the first few days after germination is an issue, for example with bacterial and fungal root and collar rots), then at any stage after that, depending on the timing required for a plant to grow in order to evidence a discriminatory benefit that enables it's selection from the plant population (for example, to discriminate say the top 10 of 200 plants).

The inventor(s) has observed that different microorganisms may associate with a plant at different stages of the plant's life. Accordingly, harvesting a plant at different time points may result in selection of a different population of microorganisms. Such microorganisms may be of particular benefit in improving plant condition, survival and growth at critical times during its life: by way of example, as mentioned herein before, a plant may be susceptible to attack by nematodes at discrete time points during its life and the invention may be used to identify and isolate a population of microorganisms which may increase resistance to such attack at that particular life stage.

In another embodiment of the invention, in the case of microorganisms that form an association with a plant that allows vertical transmission from one generation or propagule to the next (for example seed-endophytic or -epiphytic associations, or endophytic and epiphytic associations with plants/propagules multiplied vegetatively) the microorganisms may not be isolated from the plant(s). At the conclusion of a method of the invention a target or selected plant itself may be multiplied by seed or vegetatively (along with the associated microorganisms) to confer the benefit(s) to "daughter" plants of the next generation or multiplicative phase. Similarly, where a successive repeat of the method is desired, plant material (whole plant, plant tissue, part of the plant) comprising the set of one or more microorganisms can be used in step a) of any successive repeat.

Stacking

The inventor(s) envisage advantages being obtained by stacking selective pressures in repeated rounds of the method of the invention. This may allow for acquiring a population of microorganisms that may assist a plant in surviving in a number of different environmental conditions, resisting a number of different diseases and attack by a number of different organisms, for example.

Similarly, the inventor(s) envisage advantages being obtained by stacking the means of selection (or the selection criteria) of plants in repeated rounds of the method of the invention. This may allow for the acquisition of a population of microorganisms that may assist a plant in having a number of different desirable traits, for example.

One could also stack both selective pressures and selection criteria in methods of the invention.

In one embodiment of the invention the one or more microorganisms acquired from the one or more plants selected following exposure to a selective pressure, as previously described, is used in a second round or cycle of the method; ie the microorganisms from the selected plants are provided, along with one or more plants and a growth medium, a selective pressure is applied, plants are selected at a desired time and microorganisms are isolated from the selected plants. The microorganisms acquired from the second round of the method may then be used in a subsequent round, and so on and so on.

In one embodiment, the selective pressure applied in each repeat of the method is different. For example, in the first round the pressure may be a particular soil pH and in the second round the pressure may be nematode attack. However, in other embodiments of the invention, the selective pressure applied in each round may be the same. It could also be the same but applied at differing intensities with each round. For example, in the first round the selective pressure may be a particular concentration of salt present in the soil. In the second round, the selective pressure may be a higher concentration of salt present in the soil. In one embodiment, the selective pressure is increased in successive rounds in a pattern that may be linear, stepped or curvilinear. For example in round 1 of an iterative selective process wheat plus microorganisms may be exposed to 100 mM NaCl, in the second to 110 mM salt, in the third to 120 mM salt, thus increasing the selective pressure on the plants as adaptation occurs via improved plant/microorganism associations. Alternatively, it may be advantageous to maintain a selective pressure of 120 mM for several rounds to allow for a slower adjustment in the microbial population balance underlying improvements in the ability of wheat to grow productively in a higher salt environment.

In one embodiment, a selective pressure may be separated disjunctively from a specific step of the iterative process, particularly the first round of an iterative cycle. For example in round one the selective pressure may not be applied at all. But after the microorganisms have been isolated from the selected plants after exposure for a relevant period to a growth medium and microorganisms in round 1, they are applied to the plant growth medium along with the plant, seed, seedling, cutting, propagule or the like for round 2. After an appropriate time a selective pressure is applied in round 2 and in successive rounds. This type of selection may be especially relevant for selection factors that severely diminish the plant tissue that is the target of the selection. For example nematodes are especially destructive of root tissue and it may be advantageous to allow particular microbes to multiply to high levels on, in, or around the roots in round 1 to allow high concentrations of microorganisms from the roots of plants selected in round 1 to be applied to the growth medium in round 2.

Where selection criteria are stacked, the one or more microorganisms acquired from the one or more plants selected, as previously described, is used in a second round or cycle of the method, where a different selection criterion is used. For example, in the first round, one or more plants may have been selected based on biomass. In the second round, one or more plants may be selected based on production of a particular compound. The microorganisms from the second round of the method may then be used in a subsequent round, and so on and so on. Any number of different selection criteria may be employed in successive rounds of the method, as desired or appropriate.

In one embodiment, the selection criteria applied in each repeat of the method is different. However, in other embodiments of the invention, the selection criteria applied in each round may be the same. It could also be the same but applied at differing intensities with each round. For example, the selection criteria may be fibre levels and level of fibre required for a plant to be selected may increase with successive rounds of the method. The selective criteria may increase or decrease in successive rounds in a pattern that may be linear, stepped or curvilinear.

It should be appreciated that the methods of the first and second (and/or related) aspects of the invention may be combined such that they alternate. For example, a method of the first aspect is performed and the microorganisms acquired in that method used in step a) of a method of the second (and/or related) aspect of the invention. The microorganisms acquired in step d) of a method of the second (and/or related) aspect of the invention may then be used in step a) of a method of the first aspect. This may be repeated any number of times as necessary or desired. It should be appreciated that the methods may be combined in any order and in any combination or permutation. For example, they need not alternate on a one by one basis. Any number of repeats of one a method of one aspect may be performed before switching to one or more round of a method of the other aspect. The methods of the first and second (and/or related) aspect may also be run independently and then the microorganisms acquired in the methods combined and used in a further round of one or both methods, and so on.

It should also be appreciated that in certain embodiments of the invention, where one or more microorganism(s) forms an endophytic or epiphytic relationship with a plant that allows vertical transmission from one generation or propagule to the next the microorganisms need not be isolated from the plant(s). At the conclusion of a method of the invention a target or selected plant itself may be multiplied by seed or vegetatively (along with the associated microorganisms) to confer the benefit(s) to "daughter" plants of the next generation or multiplicative phase. Similarly, where a successive repeat of the method is desired, plant material (whole plant, plant tissue, part of the plant) comprising the set of one or more microorganisms can be used in step a) of the successive repeat.

It should further be appreciated that two or more selective pressures and/or two or more selection criterion may be applied with each iteration of a method of the invention.

Conditioning and Directed Evolution

As outlined previously herein, the methods of the invention include a step of subjecting either or both of the first set of one or more microorganisms and the second set of one or more microorganisms to a conditioning and/or directed evolution process. This may occur prior to step a) at the beginning of a method of the invention and/or after step d) and prior to step a) of any successive repeat of the method steps. It may also occur after step d) at the conclusion of a method of the invention. It may also be repeated two or more times if appropriate.

A "conditioning process" as used herein should be taken broadly to include any process which promotes a microorganism to grow, proliferate, improve colonisation of plant tissues (including the rhizosphere), assume a specified morphology or physiological status, express one or more protein, produce one or more metabolite or other compound which may assist the one or more microorganism in imparting one or more beneficial property to one or more plant.

A conditioning process may involve subjecting the one or more microorganism to one or more media containing one or more ingredient that is known to promote a microorganism to grow, proliferate, or promote or activate a particular pathway for the production of one or more compound or the like. For example, a microorganism may be conditioned for improved colonization of plant tissues of the rhizosphere through growth on specialised media. By way of further example, microorganisms may be conditioned by growth on plant tissue culture media such as Murashige and Skoog medium (Murashige T and Skoog F (1962) A revised medium for rapid growth and bioassays with tobacco tissue cultures. Physiol Plant 15(3): 473-497). Culture may be performed with or without co-culture of plant material. A conditioning process may also involve manipulation of growth conditions to elicit a specific physiological trait such as heat shock or cold shock response, sporulation, stationary phase induction or germination, or to coordinate the growth status of a population for example through continuous culture.

A "directed evolution process" as used herein should be taken broadly to include any process which promotes the evolution of the one or more microorganism. Such evolution may be controlled or random. For example, the microorganism may be subjected to targeted genetic modification or random genetic modification. By way of example techniques such as site directed mutagenesis, gene shuffling, whole genome shuffling, random mutagenesis by way of transpositional insertion, UV irradiation, application of chemical mutagens and the like may be used to introduce mutations or genetic variation to the population of one or more microorganisms. By way of further example, microorganisms may be genetically modified to include specific heterologous nucleic acids or knock out nucleic acids native to the microorganisms to affect a specific change; such as expression of a particular gene or suppression of a particular gene, or to affect a change to the gene product. The directed evolution may allow for the generation of microorganisms having superior properties of use in the invention.

The directed evolution and/or conditioning processes may involve a step of selecting and/or enriching for a subset of one or more microorganisms from the original population of microorganisms subjected to either or both processes. Such selecting and enrichment steps may include, by way of example, growth of the microorganisms on particular selective media, pasteurisation steps, analysis of one or more phenotypic and/or genotypic traits including levels of one or more compounds produced by the microorganisms, including metabolites, the nature and or expression levels of one or more proteins, presence of one or more genetic markers. A selective process may also involve growing cultures under a selective pressure designed to select for spontaneous mutations that confer a physiological trait. For example selection for microbes that are able to use a component of plant root exudates, such as glycerol, as a sole carbon source.

The analysis of phenotypic and/or genotypic traits of the microorganisms may be completed using any number of known techniques. However, by way of example the following techniques may be employed: including but not limited to high through-put screening of chemical components of plant, sequencing techniques, including high through-put sequencing of genetic material, differential display techniques (including DDRT-PCR, and DD-PCR), nucleic acid microarray techniques, RNA-seq (Whole Transcriptome Shotgun Sequencing), qRT-PCR (quantitative real time PCR).

The results of the analysis of phenotypic and/or genotypic traits of the microorganisms may be compared to information contained on one or more database, which may assist in the selection of a subset of microorganisms of use in a method of the invention. For example, certain genetic profiles, expression profiles, metabolic profiles and the like may be known to be associated with certain properties and one may be able to select the best microbial candidates on basis of this information.

Microorganisms and Compositions Containing Same

In addition to the methods described herein before, the invention relates to microorganisms selected, acquired or isolated by such methods and compositions comprising such microorganisms. In its simplest form, a composition comprising one or more microorganisms includes a culture of living microorganism, or microorganisms in a live but inactive state(s), including frozen, lyophilised or dried cultures. However, the compositions may comprise other ingredients, as discussed below.

The invention should also be understood to comprise methods for the production of a composition to support plant growth, quality and/or health, or a composition to suppress or inhibit plant growth, quality and/or health, the method comprising the steps of a method herein before described and the additional step of combining the one or more microorganisms with one or more additional ingredients.

A "composition to support plant growth, health, and/or quality" should be taken broadly to include compositions which may assist the growth, general health and/or survival of a plant, the condition of a plant, or assist in the maintaining or promoting any desired characteristic, quality, and/or trait. It should be taken to include maintaining or altering the production of one or more metabolite or other compound by a plant as well altering gene expression and the like. The phrase should not be taken to imply that the composition is able to support plant growth, quality and/or health on its own. However, in one embodiment the compositions are suitable for this purpose. Exemplary compositions of this aspect of the invention include but are not limited to plant growth media, plant mineral supplements and micronutrients, composts, fertilisers, potting mixes, insecticides, fungicides, media to protect against infection or infestation of pests and diseases, tissue culture media, see coatings, hydroponic media, compositions that impart tolerance to drought or abiotic stress such as metal toxicity, compositions that modify soil pH.

A "composition to inhibit or suppress plant growth, health, and/or quality" should be taken broadly to include compositions which may assist in suppressing or inhibiting one or more characteristic or quality and/or trait of a plant, including its growth, general health and/or survival. It should be taken to include maintaining or altering the production of one or more metabolite or other compounds by a plant as well altering gene expression and the like. The phrase should not be taken to imply that the composition is able to suppress or inhibit plant growth, quality and/or health on its own. However, in one embodiment the compositions are suitable for this purpose. Exemplary compositions of this aspect of the invention include but are not limited to plant growth suppression media, weed killer, fertilisers, potting mixes, plant mineral supplements and micronutrients, composts, mixes, insecticides, fungicides, tissue culture media, seed coatings, hydroponic media, compositions that impart tolerance to drought or abiotic stress such as metal toxicity, compositions that modify soil pH.

Skilled persons will readily appreciate the types of additional ingredients that may be combined with the one or more microorganisms, having regard to the nature of the composition that is to be made, the microorganisms to be used, and/or the method of delivery of the composition to a plant or its environment. However, by way of example, the ingredients may include liquid and/or solid carriers, microbial preservatives, microbial activators that induce specific metabolic activities, additives to prolong microbial life (such as gels and clays), wettable powders, granulated carriers, soil, sand, agents known to be of benefit to microbial survival and the growth and general health of a plant, peat, organic matter, organic and inorganic fillers, other microorganisms, wetting agents, organic and inorganic nutrients, and minerals.

Such compositions can be made using standard methodology having regard to the nature of the ingredients to be used.

Compositions developed from the methods of the invention may be applied to a plant by any number of methods known to those skilled in the art. These include for example: sprays; dusts; granules; seed-coating; seed spraying or dusting upon application; germinating the seed in a bed containing suitable concentrations of the composition prior to germination and planting out of the seedlings; prills or granules applied next to the seed or plant during sowing or planting, or applied to an existing crop through a process such as direct drilling; application to plant cuttings or other vegetative propagules by dipping the cut surface or the propagule into liquid or powdered microbial substrate prior to planting; application to the soil as a "soil treatment" in the form of a spray, dust, granules or composted composition that may or may not be applied with plant fertilisers prior to or after sowing or planting of the crop; application to a hydroponic growth medium; inoculation into plant tissues under axenic conditions via injection of compositions or otherwise inoculated via a cut in such tissues, for the subsequent establishment of an endophytic relationship with the plant that extends to the seed, or propagative tissues, such that the plant can be multiplied via conventional agronomic practice, along with the endophytic microbe providing a benefit(s) to the plant.

Methods of Producing Alternative Compositions

When microorganisms are cultured they may produce one or more metabolites and which are passed into the media in which they reside. Such metabolites may confer beneficial properties to plants.

Accordingly, the invention also provides a method of for selecting or producing a composition capable of imparting one or more beneficial property to a plant, for example to support plant growth, quality and/or health, or for example to suppress or inhibit growth, quality and/or health of a plant, or to identify microorganisms that are capable of producing such a composition. In one embodiment, the composition is substantially free of microorganisms.

In one embodiment, the method is for the selection of a composition the method comprising at least the steps of:
a) culturing one or more microorganisms selected by a method of the first aspect and/or a method of the second (and/or related) aspect in one or more media to provide one or more culture;
b) separating the one or more microorganism from the one or more media in the one or more culture after a period of time to provide one or more composition substantially free of microorganisms;
c) subjecting one or more plant (including for example seeds, seedlings, cuttings, and/or propagules thereof) to the one or more composition of step b);
d) selecting one or more composition from step c) if it is observed to impart one or more beneficial property to the one or more plants.

In another embodiment, the method is for the selection of a composition and comprises at least the steps of:
a) culturing one or more microorganisms selected by a method of the first aspect and/or a method of the second (and/or related) aspect of the invention in one or more media to provide one or more culture;
b) inactivating the one or more culture of step a) to provide one or more composition containing one or more inactivated microorganisms;
c) subjecting one or more plant (including for example seeds, seedlings, cuttings, and/or propagules thereof) to the one or more composition of step b);
d) selecting one or more composition from step c) if it is observed to impart one or more beneficial property to the one or more plants.

In another embodiment, the method is for the selection of one or more microorganisms which are capable of producing a composition and comprises at least the steps of:
a) culturing one or more microorganism selected by a method of the first aspect and/or a method of the second (and/or related) aspect in one or more media to provide one or more culture;
b) separating the one or more microorganism from the one or more media in the one or more culture from step a)

after a period of time to provide one or more composition substantially free of microorganisms;

c) subjecting one or more plant (including for example seeds, seedlings, cuttings, and/or propagules thereof) to the one or more composition from step b);

d) selecting the one or more microorganisms associated (or in other words used to produce the) with one or more composition observed to impart one or more beneficial property to the one or more plants.

Another method of the invention comprises at least the steps of:

a) culturing one or more microorganism in one or more media to provide one or more culture;

b) separating the one or more microorganism from the one or more media in one or more culture after a period of time to provide one or more composition substantially free of microorganisms;

c) subjecting one or more plant (including for example seeds, seedlings, cuttings, and/or propagules thereof) to the one or more composition of step b);

d) selecting the one or more microorganisms associated (or in other words used to produce the) with one or more composition observed to impart one or more beneficial property to the one or more plants; and, e) using the one or more microorganisms selected in step d) in step a) of a method of the first or second or eighth or ninth aspects of the invention.

In another embodiment, step b) of the method of the previous two paragraphs could be substituted with the step of b) inactivating the one or more culture of step a) to provide one or more composition containing one or more inactivated microorganisms, and then using this composition in step c) of the process.

As used herein "inactivating" the one or more culture and "inactivated microorganisms" and like terms should be taken broadly to mean that the microorganisms are substantially inactivated, fixed, killed or otherwise destroyed. The term should not be taken to mean that all microorganisms are inactivated, killed or destroyed, however, this may be preferable. In one embodiment, the microorganisms are inactivated, fixed, killed or otherwise destroyed to the extent that self-sustained replication is no longer measurable using techniques known to one skilled in the art.

The microorganisms can be inactivated, killed, fixed or destroyed using any appropriate techniques known in the art. However, by way of example, one may use chemical agents and/or physical means to do so. In one embodiment, the cells are lysed. In another embodiment cells are fixed by chemical means, so as to render the organisms non-viable, but retaining their structural integrity.

As used herein, a "composition substantially free of microorganisms" should be taken broadly and not be construed to mean that no microorganisms are present, although this may be preferred.

In certain embodiments of these methods, microorganisms are cultured in two or more (preferably a large number, for example, from at least approximately 10 to up to approximately 1000) mixed cultures using media that can support the growth of a wide variety of microorganisms. Any appropriate media known in the art may be used. However, by way of example, growth media may include TSB (tryptic soy broth), Luria-Bertani (LB) broth, or R2A broth. In another embodiment, selective or enrichment media which are able to support the growth of microorganisms with an array of separate but desirable properties may be used. By way of example, the enrichment media referred to elsewhere herein may be used.

The microorganisms may be cultured in the media for any desired period. Following culture, the microorganisms are separated from the media and stored for later use. A separate composition also results. One or more plants in a suitable growth medium are then subjected to the composition (using any known methodology, or methodology as described herein before). After a period of time, growth of plants is assessed and plants selected (as described herein before, for example). Plants are preferably selected on the basis of size. However, other selection criteria as referred to herein may be used.

In one embodiment, the microorganism(s) producing the subset of compositions associated with the selected plants are recovered from storage. Two or more separate cultures of the microorganisms may then be mixed together and separated into two or more sub-cultures grown in two or more different media.

This process can be repeated iteratively as many times as is deemed efficacious, with progressive steps refining down to fewer media and a narrower diversity of microorganisms until a desirable effect on the growth plants is achieved with a mixture of microbes that can be identified, grown and stored indefinitely as a standard starting inoculum for the production the composition.

Compositions of this aspect of the invention may be used or formulated on their own or combined with one or more additional ingredients.

It should be appreciated that the general methodology described herein before may be applicable to this aspect of the invention, including but not limited to growth media, plants, microorganisms, selective pressures, timing, iterative processing, and combinations thereof.

Additional Methodology

The following methodology may be applied to a method of the invention for identifying one or more microorganisms as herein before described.

FIG. 1 shows a system 10 according to an embodiment of the invention. System 10 includes requestors 11, request processor 12, growing facility 13, database or library 14 and depository 15.

FIG. 2 provides a flow chart illustrating a method 20 according to an embodiment of the invention. The steps shown in FIG. 2 will be described with reference to the system 10 shown in FIG. 1.

This aspect of the invention is described in terms of identifying one or more microorganism that may impart one or more desired properties to one or more plants, with particular reference to the first, second, eighth (and/or related) and/or ninth (and/or related) aspects of the invention. However, it should be appreciated that it is equally applicable to the identification of one or more compositions that may impart one or more desired property to one or more plant, or one or more microorganism that produces a composition that may impart one or more desired property to one or more plant, as herein before described, and summarised in the eighth (and/or related) and ninth (and/or related) aspects of the invention. Accordingly, unless the context requires otherwise, when describing the embodiments of the invention in this section of the specification, reference to the first aspect of the invention should be taken to also include reference to the second (and/or related), eighth (and/or related) and/or ninth (and/or related) aspects of the invention, and reference to one or more microorganism should be taken to include reference to one or more composition.

The method begins at step 21 with a requestor 11 identifying a plant (or a class or group of plants). Reasons why particular plants or types of plants may be identified will be apparent to those skilled in the art. However, by way of example, it may have been found that a plant noted in general for having a high growth rate is growing at lower rates or not at all, there may simply be a desire to improve on existing growth rates or there may be a desire to introduce a plant to a different climate/environment/geographical region. The invention is not limited to conferring improvements to particular plant(s) and may be used to inhibit growth or otherwise adversely affect the plant(s).

At step 22, the requestor 11 sends the plant and/or the identity thereof to a request processor 12. The requestor 11 may provide further relevant information such as why or what properties they are seeking to improve. While only one request processor 12 is shown, it will be appreciated that more than one may be provided in the system 10.

Where a requestor 11 identifies a class or group of plants, more than one plant variety may be evaluated. Alternatively or additionally, selection of a one or more plant variety may be made elsewhere within the system 10 based on the group or class identified, including following evaluation of different varieties including using different microorganisms in accordance with methods of the invention.

Requests may conveniently be received over the internet via a web browser, although the invention is not limited thereto. Use of a web browser may additionally or alternatively be used to enable a requestor 11 to view reports on the progress being made in response to their request. For example, measures of growth may be provided.

At step 23, the request processor 12 receives and processes the request, essentially by initiating the performance of the method for the selection of one or more microorganism according to the first aspect of the invention. Note that the request processor 12 may or may not actively perform the method of the first aspect, or may only perform parts thereof. According to particular embodiments, the request processor 12 may act as an intermediary or agent between the requestor 11 and the parties able to perform the method of the first aspect. Also, different arrangements may be made in response to different requests. For example, for one request, the environment around the request processor 12 may be suitable for evaluating a particular plant but unsuitable for another, requiring the assistance of a third party facility. This could be due to a desire to test in a particular soil type, altitude or climate. Other factors will also be apparent although it is appreciated that "artificial" environments may be used. Furthermore, varying degrees of user interaction may take place at the request processor 12. According to one embodiment, a computer processor selects parameters or conditions for a study based on data input by a requestor 11. As will be appreciated, providing a structured information request may help to effect this, and where necessary, reference may be made to databases including database 14.

At step 24, parameters of the evaluation process are selected. For example, reference may be made to database 14 for microorganisms that may provide the desired improvement in the plant(s). While little data to date has been provided in the art on microorganisms having beneficial associations with particular plant varieties, this will be improved upon through ongoing operation of the methods of the invention and stored in database 14. Other parameters such as plant type(s) and environmental conditions may also be selected.

At step 25, the request (or portions thereof) and evaluation parameters are sent to growing facility 13 which may obtain suitable microorganisms from depository 15. These may or may not have been previously identified. While only one growing facility 13 and one depository 15 are shown, it will be appreciated that the invention is not so limited. Furthermore, any two or more of request processor 12, growing facility 13, database 14 and depository 15 may be co-located and/or under the same control.

At step 26, a selection process is performed, preferably according to the selection method of the first aspect.

At step 27, a response is sent to the request. A response may be sent to the requestor 11 and/or to a third party and preferably includes at least one of at least a subset of the results generated at step 26, identification of plant(s), plant(s), identification of microorganism(s), microorganism(s), or plant(s) provided in association with microorganisms, namely those that have been shown to provide benefits at step 26.

At step 28, database 14 may be updated with results of the selection process of step 26. This step may be performed prior to step 27, including periodically or at other various stages which the selection process is conducted. Preferably, at least details of new beneficial associations between plant(s) and microorganisms are recorded. It will be appreciated that incompatible or less beneficial associations will also preferably be recorded, thereby over time building a knowledge framework of plants and microorganisms.

It will be appreciated that one or more of the steps of FIG. 2 may be omitted or repeated. For example, growing facility 13 may generate results at step 26 and in response thereto, one or more of steps 21 to 26 may be repeated.

Thus, the invention provides means and methods to improve plant(s) (or growth or other characteristics thereof). This is achieved by enabling a requestor 11 in a first geographical region (e.g. country) or otherwise defined environment (e.g. by parameters or characteristics affecting growing conditions such as such soil salinity or acidity) to access microbiological biodiversity not present or of limited presence in the first region for the purposes of plant improvement in the first or another region. The other region may be or in a foreign country but may be otherwise defined by characteristics of that environment that affect a plant rather than being defined by political boundaries. Consequently, the invention may enable a requestor to obtain the beneficial effects of a particular microorganism(s) on a particular plant(s) in a first region, even though such microorganism(s) may not be present or are of limited presence in the first region.

An example implementation of the invention is provided below.

1. A company in say New Zealand (home company), enters into a contractual relationship with a second, say overseas, company (overseas company).
2. The overseas company agrees to send seeds, cuttings or other plant propagules (foreign cultivar) to the home company from plant cultivars adapted to the environment(s) in its own, or other foreign countries, in order to gain access to elements of New Zealand's terrestrial and marine microbial biodiversity that are able to form beneficial plant-microorganism associations with the foreign cultivar.
3. The nature of the benefit may encompass increased plant productivity, for example through any one or more of but not limited to: increased root or foliar mass, or through an increase in efficiency in nutrient utilisation through nitrogen fixation by diazatrophs such as *Klebsiella* or *Rhizobium*, or through release of plant nutrients from the soil, such as phosphates released soil through the production of microbial phytases, or through improved resistance to attack from pests and diseases spanning a broad range of nematodes, insects, microbial and virus diseases, or through improvements in the ability of the plant to resist adverse environmental conditions such as drought, salinity, extreme temperatures, toxic soil minerals, or through improvements in plant phenotype for example date of flowering, or changes in physical form e.g. colour frequency of root or foliar branching, or changes in chemical profile including compounds associated with taste, smell or properties which make the plant suitable for a particular purpose.

4. In New Zealand, the home company identifies which indigenous microorganisms can form an association with the foreign plant by exposing the seed to the microorganisms, with or without knowledge of their likely effects on the plant, by the method of germinating the seed and growing the plant in a growing material that ensures contact of the plant during its growth with indigenous microorganisms via seed coating, direct inoculation into the seed or germinating seedling and/or contamination of the growing medium. The invention is not limited to this arrangement or methodology. For example, it may be apparent that microorganisms present in soil other than in New Zealand may provide benefits and testing may be conducted in such regions in addition to or instead of New Zealand. Also, artificial environments may be created. Referring to the immediately prior example, this may be achieved by obtaining soil and/or microorganisms from such regions and conducting the tests in say New Zealand. As will be apparent, such embodiments may include provision for artificial control of climatic conditions among other parameters. Thus, the invention is not limited to conducting testing in a region based on its indigenous microorganisms—the microorganisms may be artificially introduced so as to conduct the testing elsewhere than in the microorganisms' natural environment.

5. The period of growth and the physical conditions under which they take place may vary widely according to plant species and specific plant improvement traits, including based on parameters desired or specified by the overseas company.

6. After the relevant period of plant growth the nature of possible plant-microorganisms associations may be determined by microbiological assessment to determine whether microorganisms have formed an endophytic, epiphytic or rhizospheric association with the foreign crop.

7. Where such association(s) are demonstrated the microorganisms form a collection of (say New Zealand indigenous) microorganisms able to associate with the (say foreign) crop or plant.

8. In one embodiment of the invention, microbial isolates of the collection may, for example, be coated on to seeds, inoculated into seeds or seedlings, or inoculated into a growing medium that may or may not be sterile.

9. After a suitable period the plants are assessed for improved root and foliar growth or other desired characteristics and/or they may be exposed to environmental stressors designed to identify the plant-microorganism associations most able to provide benefit to the plant in the manner desired by the overseas company.

10. Examples of such stressors or selection criteria are provided in 3 above and elsewhere herein, and where identical pests, diseases or other parameters of the second, overseas environment are not present in the home or test region (i.e., New Zealand in the example), similar microbial diseases, nematode and insect pests or other parameters most similar to those in the overseas environment and that may be considered acceptable to the overseas company may be selected. As mentioned in 4 above, the invention also includes introducing foreign material or creating otherwise artificial conditions in the home or test region.

11. The steps involving growing one or more plant in the presence of one or more microorganism, selecting one or more plants with desired characteristics, and acquiring the microorganism(s) forming an association with the plant will be repeated one or more time.

12. One or more conditioning and/or directed evolution step in accordance with the invention is performed at the appropriate time (such as after selection of plants and acquisition of the one or more microorganism(s) forming an association with the one or more plants) by any appropriate party.

13. Elite microorganisms providing commercially-significant benefit to the growth of the foreign cultivar are identified by this process and may be shipped to the overseas company for further testing and selection in the foreign environment.

14. In a further embodiment the overseas company will agree that microorganisms found on, or in, the seed, cuttings or propagules of the foreign cultivar will be added to the collection of the home company to enlarge the collection for use both on that cultivar or on other foreign cultivars received for similar testing from other companies.

In an alternative embodiment, the microbial isolates able to form plant-microorganism associations with the foreign cultivar i.e., the collection, are sent to the second company for testing and selection, such that items 8-11 above are performed by and/or in the grounds of the second company. This may be performed by or under the control of the first company.

As a further alternative, rather than identifying and using predetermined microorganism(s) of a collection, the home company may simply expose the seed to indigenous microorganisms, with or without knowledge of their likely effects on the plant, for example by germinating the seed and growing the plant in a growing material that ensures contact of the plant during its growth with indigenous microorganisms via seed coating, direct inoculation into the seed or germinating seedling and/or contamination of the growing medium or otherwise. As will be apparent, the home company may additionally or alternatively arrange for similar testing in other regions, where the same or different microorganisms may be present. The period of growth and the physical conditions under which they take place may vary widely according to plant species and specific plant traits desired by the overseas company. After a period of plant growth the nature of possible plant-microorganism associations may be determined in a similar manner to that described above.

EXAMPLES

The invention is now further described by the following non-limiting examples.

Transgenic plants expressing beneficial traits such as insect-resistance or herbicide resistance have been widely adopted by both farmers in North and South America and Asia. It would be desirable to extend the benefits of traits similar to those expressed by transgenic crops, as well as other beneficial crop traits, without the need for engineering the plant genome. In the method outlined below we exemplify the potential of combining whole genome shuffling of microbes mediating beneficial crop trait(s) with the use of methods to select plant/microorganism relationships to direct the selection of shuffled strains for close association with a specific crop in order to confer it with a desired trait(s).

Example 1: Use of a Method of the Invention Combined with Whole Genome Shuffling to Select Corn-Adapted Bacteria Conferring Resistance to the Corn Root Worm Step 1: Library Acquisition Whole genome shuffling can accelerate directed evolution by facilitating recombination between the members of a selected population of microbes. Diverse strains of *Bacillus thuringiensis* containing Cry3 genes and other cry genes with activity against the corn root worm (CRW) have been found in numerous habitats. Similarly, multiple species and strains of *Bacillus*, including *B. thuringiensis*, have been found in endo-, epi- or rhizospheric association with many crop species, including corn. Multiple strains from both of these sources, i.e. both CRW active and corn-root associative are combined to form a single parental library.

Step 2: Recombination of Bacterial Genomes

Combinatorial libraries of new strains are generated from the parental library by intraspecific fusion and interspecific hybridization by methods familiar to those skilled in the art, including protoplast fusion, electroporation or any other method inducing competence. In some applications strains from the parental library may be mutagenized to create additional variability. Recombinant strains are then regenerated, resulting in a combinatorial strain library. This library may then be pooled and subjected to further rounds of recombination and regeneration to create still further variability.

Step 3: Strain Selection (SS)

Regenerated combinatorial strains resulting from step 2 are subjected to an iterative process to select strains that are both adapted to corn roots and express the anti-CRW trait.

SS Step 1:

strains (initially from the combinatorial library) are preferably pooled and applied to a plant growth medium or soil into which corn seeds are planted. Alternatively, the microorganism(s) are mixed into a suitable seed coating material e.g. a gel, and coated onto seeds before being planted into a similar plant medium. Alternatively, the seeds are geminated and then exposed to the microorganisms for a short period (usually between 1-24 hours to maximise the chance that the microbes may form an endophytic or epiphytic association with the germinating plant) and then planted into a similar growth medium. In each of these cases the growing medium may be initially sterile, although this is not essential and further microorganisms applied to the growth medium and/or plant.

SS Step 2:

After a suitable period of time, preferably 2-4 weeks, the plants are harvested and the roots removed. Preferably, roots are surface sterilized using low concentrations of ethanol and/or sodium hypochlorite and other procedures well known to those skilled in the art. Endophytic bacterial strains are then isolated from root tissue and either microscopically examined for the desired phenotype i.e. presence of characteristic Cry3 protein crystals, or characterised genetically for the possession of genetic markers linked to Cry3 genes. Alternatively, isolated strains are grown in pure culture and assayed in vivo for bioactivity against CRW larvae. As a further option, endophytic strains selected for desired properties may be subjected to a further round(s) of recombination, regeneration and selection to create a new library of strains enriched for an improved likelihood of colonising root tissue and killing CRW larvae.

A materially different approach to strain selection does not require microbial isolation. Instead in this example the inventor(s) create bacterial suspensions from root-crushes of surface-sterilised roots (endophytes) or washed roots (epi- and endo-phytes) or from suspensions from rhizospheric microbes. Small fractions are assayed comparatively for activity against CRW larvae. Preparations represented by the most active fractions are selected use in a further round(s) of selection.

Alternatively, the corn plants may not be harvested, but exposed to a uniform CRW selection pressure by the addition of standard numbers of CRW larvae to the plant growth medium. After a suitable period of time the plants may be removed from the growth medium and the degree of root damage assessed. Plants displaying the least damage are selected and bacteria associated with the roots are either isolated and assessed for CRW activity as above (or not), or prepared as root crushes from the least damaged plants.

SS Step 3:

microbial isolates and/or root crushes selected in step 2 are added to the plant growth medium, either individually or pooled (preferably) into which, preferably, surface-sterilized corn seeds are planted. Alternatively, the microorganism(s) are mixed into a suitable seed coating material e.g. a gel, and coated onto the seeds before being planted into a similar plant medium. Alternatively, the seeds are geminated and then exposed to the microorganisms for a short period (usually between 1-24 hours to maximise the chance that the microbes may form an endophytic or epiphytic association with the germinating plant) and then planted into a similar growth medium. In each of these cases the growing medium may be initially sterile, although this is not essential and further microorganisms applied to the growth medium and/or plant.

The process from step 2 to step 3 may then be repeated iteratively, with or without modification of the selection criteria for CRW.

Step 4: After this iterative process has been conducted to the point at which improvement of root-associated (either endophytic, epiphytic or rhizospheric) microbial activity against the CRW is deemed to be sufficient, the best-performing strains are selected again as in step 2, or bacteria are finally isolated as in step 2 from the best performing root crushes or similarly isolated from roots of the plants most resistant to CRW attack. These microorganisms are both active against CRW larvae and adapted to close association with corn roots and can be used to develop commercial products such as seed coatings or granules applied at planting that impart a trait for corn root worm resistance to corn.

Example 2: Use of a Method of the Invention with Directed Molecular Evolution to Select Corn-Adapted Bacteria Conferring Desirable Crop Output Traits Directed evolution of single genes or loci through random or directed mutagenesis techniques and other recombinatorial procedures known to those skilled in the art, can be used to create libraries of microbes exhibiting targeted genetic variation. In this example the process outlined in the invention is applied as a series of iterative steps following creation of the library, to generate crop-adapted strains of microbes conferring the desired phenotype. The methodology is as generally described above with the difference being that specific genes or loci associated with a desired phenotype are targeted.

Recombinant libraries may be used separately or combined with naturally-occurring microbes derived from any material or step in a process of the invention.

Example 3: Use of Process to Select Seed-Borne Endophytes Conveying a Beneficial Crop Trait Forage grasses expressing beneficial traits such as insect-resistance and improved tolerance to both biotic and abiotic stressors via strains of the seed-borne fungus *Neotypodium* sp. have been widely adopted by farmers in Zealand and elsewhere. It would be desirable to extend the benefits of traits similar to those expressed by this seed-borne fungus and other similar species in the fungal family, to a broader range of seed-borne endophytic microbes thereby providing access to a much wider range of beneficial crop traits.

Step 1. Untreated ryegrass seeds are planted in a wide variety of soils in small pots. Soils may include additional amendments comprising pure cultures of microorganisms, mixtures of microorganisms or materials containing microorganisms that derived from other sources, including those outlined in examples 1 and 2 above.

Step 2. After a suitable period of growth, the plants are washed out of the soil, surface sterilised with a combination of ethanol and sodium hypochlorite or other methods known to people skilled in the art, and the endophytic microorganisms (endophytes) isolated from internal tissues of roots and stems/foliage and seeds, either as individual isolates in pure culture, or as mixed populations e.g. as a microbial suspension from an aqueous root crush and/or a stem/foliar crush.

Step 3. The endophytic microorganisms are then added to a plant growth medium into which pre-germinated surface-sterilised ryegrass seeds are planted (seeds checked for sterility by germinating on nutrient agar plates). Alternatively, the microorganism(s) are mixed into a suitable seed coating material e.g. a gel, and coated onto surface-sterilised seeds before being planted into a similar plant medium. Alternatively, the surface-sterilised seeds are geminated on nutrient agar plates, checked for sterility and then exposed to the microorganisms for a short period (usually between 1-24 hours to maximise the chance that the microbes may form an endophytic or epiphytic association with the germinating plant) and then planted into a similar growth medium. In each of these cases the growing medium may be initially sterile, although this is not essential and further microorganisms may be applied to the growth medium and/or plant.

Step 4). After a period of suitable growth, e.g. 4-6 weeks, plants are assessed for expression of the desired phenotype. Phenotypes may include relative resistance to abiotic selection pressures such as relative growth in nutrient deficient conditions e.g. nitrogen or phosphorus, growth in a medium high in salinity or deficient in water. The selection pressures could also be biotic such as exposure to insect pests, plant parasitic nematodes, or plant diseases. Alternatively no selection pressure may be applied and the plants selected merely on a phenotypic attribute such as improved colour, plant form, metabolite expression, or the like.

Step 5). Selected plants are permitted to grow onward to the point of seed set. At this stage a subset of seeds from each plant may be screened for endophyte carriage using culture dependent or independent methods. The remaining seeds from plants yielding positive results in the screen are germinated and planted without microbial addition in a further round of selection to enrich for endophyte carriage and the ability to transmit the desired phenotype as described in steps 3-5.

Alternatively, endophytic microbes may be acquired from a subset of seeds from each plant either as isolates from surface sterilised seeds or as explants, or as a microbial suspension prepared, for example, by crushing the surface sterilised seed in aqueous solution. Isolates and preparations are used as an inoculum for plants arising from surface sterilised seeds as described in step 3.

In a further variation of the method, the selection for seed transmission of the trait may take place in the following generation by surface sterilising a subset of seeds (with or without prior screening) from the selected plants of the prior generation and allowing them to germinate and grow on for the period at which point phenotypic screening is conducted as generally described in steps 3 and 4 (i.e. prior to seed set). Plants exhibiting the desired phenotype in this generation (i.e. by seed transmission), are selected and either tissue explants are prepared, and/or microbes isolated from plant tissues, and/or crude microbial suspensions made by crushing the surface foliage or roots in an aqueous solution. One or a combination of these preparations are used as an inoculum for further iterative rounds of growth and selection and seed harvest, as described in steps 3-5. Alternatively, the remaining seeds of plants exhibiting the desired seed-borne trait may be germinated and planted without microbial addition in a further round of selection to enrich for endophyte carriage and the ability to transmit the desired phenotype as described in steps 3-5.

Step 6). At the end of successive rounds of this iterative process, as determined by the generation of a desired seed-borne phenotype, the best seed lines are selected for commercial assessment and cultivar development.

In this example, one or more conditioning and/or directed evolution steps are employed at one or more appropriate stage of the method in accordance with the invention described herein.

The invention has been described herein, with reference to certain preferred embodiments, in order to enable the reader to practice the invention without undue experimentation. However, a person having ordinary skill in the art will readily recognise that many of the components and parameters may be varied or modified to a certain extent or substituted for known equivalents without departing from the scope of the invention. It should be appreciated that such modifications and equivalents are herein incorporated as if individually set forth. In addition, titles, headings, or the like are provided to enhance the reader's comprehension of this document, and should not be read as limiting the scope of the present invention.

The entire disclosures of all applications, patents and publications, cited above and below, if any, are hereby incorporated by reference. However, the reference to any applications, patents and publications in this specification is not, and should not be taken as, an acknowledgment or any form of suggestion that they constitute valid prior art or form part of the common general knowledge in any country in the world.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

BIBLIOGRAPHY

Pikovskaya R I (1948). Mobilization of phosphorus in soil connection with the vital activity of some microbial species. *Microbiologia* 17:362-370

Miche, L and Balandreau, J (2001). Effects of rice seed surface sterilisation with hypochlorite on inoculated *Burkholderia vietamiensis. Appl. Environ. Microbiol.* 67(7): p 3046-3052

Fahraeus, G. (1957). *J. Gen Microbiol.* 16: 374-381

The invention claimed is:

1. A method for the selection of one or more microorganisms capable of imparting one or more beneficial properties to a plant, the method comprising at least the steps of:
   a) subjecting one or more plants to a growth medium in the presence of a first set of one or more microorganisms;
   b) selecting one or more plants following step a) on the basis of one or more phenotypic traits;
   c) acquiring a second set of one or more microorganisms associated with one or more plants selected in step b);
   d) subjecting the first set of one or more microorganisms prior to step a) and/or the second set of one or more microorganisms acquired in step c) to a targeted or random genetic modification; and
   e) repeating steps a) to d) one or more times, wherein the second set of one or more microorganisms are used in step a) of any successive repeat.

2. The method of claim 1, wherein said method is performed separately two or more times, and the one or more microorganisms acquired in step c) of each separately performed method are combined.

3. The method of claim 2, wherein the combined microorganisms are used as the first set of one or more microorganisms in step a) of any successive repeat of the method.

4. A method for the production of a composition to support plant growth, quality, and/or health; or a composition to suppress or inhibit plant growth, quality, and/or health; the method comprising the steps of claim 1 and the additional step of combining the one or more microorganisms selected by the method with one or more additional ingredients.

5. A method for the selection of a composition which is capable of imparting one or more beneficial properties to a plant, the method comprising at least the steps of:
   a) culturing one or more microorganisms selected by the method of claim 1 in one or more media to provide one or more cultures;
   b) separating the one or more microorganisms from the one or more media in the one or more cultures after a period of time to provide one or more compositions substantially free of microorganisms;
   c) subjecting one or more plants to the one or more composition of step b); and
   d) selecting one or more compositions from step c) if it is observed to impart one or more beneficial properties to the one or more plants.

6. A method for the selection of a composition which is capable of imparting one or more beneficial properties to a plant, the method comprising at least the steps of:
   a) culturing the one or more microorganisms acquired in claim 1 in one or more media to provide one or more cultures;
   b) inactivating the one or more cultures of step a) to provide one or more compositions containing one or more inactivated microorganisms;
   c) subjecting one or more plants to the one or more compositions of step b); and
   d) selecting one or more compositions from step c) if it is observed to impart one or more beneficial properties to the one or more plants.

7. A method for the selection of one or more microorganisms which are capable of producing a composition which is capable of imparting one or more beneficial properties to a plant, the method comprising at least the steps of:
   a) culturing the one or more microorganisms acquired in claim 1 in one or more media to provide one or more cultures;
   b) separating the one or more microorganisms from the one or more media in the one or more cultures from step a) after a period of time to provide one or more compositions substantially free of microorganisms;
   c) subjecting one or more plants to the one or more compositions from step b); and
   d) selecting the one or more microorganisms associated with one or more compositions observed to impart one or more beneficial properties to the one or more plants.

8. A method for the selection of one or more microorganisms which are capable of producing a composition which is capable of imparting one or more beneficial properties to a plant, the method comprising at least the steps of:
   a) culturing the one or more microorganisms acquired in claim 1 in one or more media to provide one or more cultures;
   b) inactivating the one or more cultures of step a) to provide one or more compositions containing one or more inactivated microorganisms;
   c) subjecting one or more plants to the one or more compositions from step b); and
   d) selecting the one or more microorganisms associated with one or more compositions observed to impart one or more beneficial properties to the one or more plants.

9. The method of claim 1, wherein plant material is used as the source of microorganisms for step a).

10. The method of claim 1, wherein the one or more microorganisms acquired in step c) are acquired any time after germination of the one or more plants.

11. The method of claim 1, wherein the one or more microorganisms acquired in step c) are acquired from the plant rhizosphere.

12. The method of claim 1, wherein the one or more plants are selected from seeds, seedlings, cuttings, and/or propagules thereof.

13. A method for the selection of one or more microorganisms capable of imparting one or more beneficial properties to a plant, the method comprising at least the steps of:
   a) subjecting one or more plants to a growth medium in the presence of a first set of one or more microorganisms;
   b) applying one or more selective pressures during step a);
   c) selecting one or more plants following step b) on the basis of one or more phenotypic traits; and
   d) acquiring a second set of one or more microorganisms associated with one or more plants
   selected in step c); and
wherein the first set of one or more microorganisms has been subjected to a targeted or random genetic modification prior to step a) and/or the second set of one or more microorganisms acquired in step d) are subjected to a targeted or random genetic modification.

14. The method of claim 13 further comprising the step of:
e) repeating steps a) to d) one or more times, wherein the second set of one or more microorganisms in step d) is used as the first set of one or more microorganisms in step a).

* * * * *